US009414912B2

(12) United States Patent
Gabbay

(10) Patent No.: US 9,414,912 B2
(45) Date of Patent: *Aug. 16, 2016

(54) METHOD FOR DIRECT IMPLANTATION OF A HEART VALVE PROSTHESIS

(75) Inventor: Shlomo Gabbay, New York, NY (US)

(73) Assignee: Edwards Lifesciences CardiAQ LLC, Irvine, CA (US)

(*) Notice: Subject to any disclaimer, the term of this patent is extended or adjusted under 35 U.S.C. 154(b) by 967 days.

This patent is subject to a terminal disclaimer.

(21) Appl. No.: 13/157,902

(22) Filed: Jun. 10, 2011

(65) Prior Publication Data
US 2011/0238166 A1 Sep. 29, 2011

Related U.S. Application Data

(63) Continuation of application No. 12/482,781, filed on Jun. 11, 2009, now abandoned, which is a continuation of application No. 10/266,380, filed on Oct. 8, 2002, now Pat. No. 7,803,185, which is a continuation-in-part of application No. 09/973,609, filed on Oct. 9, 2001, now Pat. No. 7,510,572, which is a continuation-in-part of application No. 09/659,882, filed on Sep. 12, 2000, now abandoned.

(51) Int. Cl.
A61F 2/24 (2006.01)
(52) U.S. Cl.
CPC .............. *A61F 2/2418* (2013.01); *A61F 2/2436* (2013.01); *A61F 2/2475* (2013.01); *A61F 2220/0016* (2013.01); *A61F 2230/005* (2013.01); *A61F 2230/0054* (2013.01); *A61F 2230/0067* (2013.01); *A61F 2230/0078* (2013.01); *G01N 2800/52* (2013.01); *Y10S 623/904* (2013.01)

(58) Field of Classification Search
CPC .. A61F 2/2427; A61F 2/2436; Y10S 623/904
USPC .............................. 623/1.24, 1.26, 2.11–2.19
See application file for complete search history.

(56) References Cited

U.S. PATENT DOCUMENTS

| 4,084,268 A | 4/1978 | Ionescu et al. |
| 4,378,224 A | 3/1983 | Nimni et al. |
| 4,477,930 A | 10/1984 | Totten et al. |
| 4,553,974 A | 11/1985 | Dewanjee |

(Continued)

FOREIGN PATENT DOCUMENTS

| EP | 1356793 | 3/2004 |
| EP | 1447111 | 8/2004 |

(Continued)

Primary Examiner — Brian Pellegrino
(74) Attorney, Agent, or Firm — Tarolli, Sundheim, Covell & Tummino LLP

(57) ABSTRACT

A method for implanting a heart valve into a patient's heart can include inserting the heart valve prosthesis into a barrel of an implanter apparatus. An opening is created in muscle tissue of the patient's heart to provide a substantially direct path that extends from the opening to a desired implantation site in the heart. A length of the barrel is inserted through the opening in the tissue such that an end of the barrel and the opening are along the direct path to the implantation site. The heart valve prosthesis is advanced through the barrel to the implantation site. The heart valve prosthesis is positioned at the desired implantation site. The heart valve prosthesis can be expanded at the desired implantation site from the reduced cross-sectional dimension toward the expanded cross-sectional dimension.

18 Claims, 13 Drawing Sheets

(56) References Cited

U.S. PATENT DOCUMENTS

| | | | |
|---|---|---|---|
| 4,573,470 | A | 3/1986 | Samson et al. |
| 4,582,181 | A | 4/1986 | Samson |
| 4,605,002 | A | 8/1986 | Rebuffat |
| 4,647,283 | A | 3/1987 | Carpentier et al. |
| 4,648,881 | A | 3/1987 | Carpentier et al. |
| 4,725,274 | A | 2/1988 | Lane et al. |
| 4,753,652 | A | 6/1988 | Langer et al. |
| 4,944,740 | A | 7/1990 | Buchbinder et al. |
| 4,955,856 | A * | 9/1990 | Phillips ............................ 600/16 |
| 5,035,706 | A | 7/1991 | Giantureo et al. |
| 5,125,895 | A | 6/1992 | Buchbinder et al. |
| 5,188,636 | A | 2/1993 | Fedotov |
| 5,304,184 | A | 4/1994 | Hathaway et al. |
| 5,306,234 | A | 4/1994 | Johnson |
| 5,320,632 | A | 6/1994 | Heidmueller |
| 5,364,408 | A | 11/1994 | Gordon |
| 5,368,601 | A | 11/1994 | Sauer et al. |
| 5,370,685 | A | 12/1994 | Stevens |
| 5,374,275 | A | 12/1994 | Bradley et al. |
| 5,397,351 | A | 3/1995 | Pavcnik et al. |
| 5,403,329 | A | 4/1995 | Hinchcliffe |
| 5,411,552 | A | 5/1995 | Anderson et al. |
| 5,417,699 | A | 5/1995 | Klein et al. |
| 5,417,700 | A | 5/1995 | Egan |
| 5,425,737 | A | 6/1995 | Burbank et al. |
| 5,431,666 | A | 7/1995 | Sauer et al. |
| 5,500,014 | A | 3/1996 | Quijano et al. |
| 5,527,322 | A | 6/1996 | Klein et al. |
| 5,537,322 | A | 7/1996 | Denz et al. |
| 5,545,214 | A | 8/1996 | Stevens |
| 5,549,665 | A | 8/1996 | Vesely et al. |
| 5,571,215 | A | 11/1996 | Sterman et al. |
| 5,713,951 | A | 2/1998 | Garrison et al. |
| 5,733,267 | A | 3/1998 | Del Toro |
| 5,792,152 | A | 8/1998 | Klein et al. |
| 5,797,960 | A | 8/1998 | Stevens et al. |
| 5,810,850 | A | 9/1998 | Hathaway et al. |
| 5,820,631 | A | 10/1998 | Nobles et al. |
| 5,840,081 | A | 11/1998 | Anderson et al. |
| 5,843,158 | A | 12/1998 | Lenker et al. |
| 5,851,210 | A | 12/1998 | Torossian |
| 5,855,597 | A | 1/1999 | Jayaraman |
| 5,855,601 | A | 1/1999 | Bessler et al. |
| 5,855,602 | A | 1/1999 | Angell |
| 5,860,990 | A | 1/1999 | Nobles et al. |
| 5,861,028 | A | 1/1999 | Angell |
| 5,891,159 | A | 4/1999 | Sherman et al. |
| 5,924,424 | A | 7/1999 | Stevens et al. |
| 5,948,017 | A | 9/1999 | Taheri |
| 5,968,068 | A | 10/1999 | Dehdashian et al. |
| 5,972,005 | A | 10/1999 | Stalker et al. |
| 6,033,378 | A | 3/2000 | Lundquist et al. |
| 6,071,273 | A | 6/2000 | Euteneuer et al. |
| 6,077,296 | A | 6/2000 | Shokoohi et al. |
| 6,106,540 | A | 8/2000 | White et al. |
| 6,117,144 | A | 9/2000 | Nobles et al. |
| 6,143,004 | A | 11/2000 | Davis et al. |
| 6,168,614 | B1 | 1/2001 | Anderson et al. |
| 6,200,336 | B1 | 3/2001 | Pavcnik et al. |
| 6,206,893 | B1 | 3/2001 | Klein et al. |
| 6,231,563 | B1 | 5/2001 | White et al. |
| 6,245,079 | B1 | 6/2001 | Nobles et al. |
| 6,251,092 | B1 | 6/2001 | Qin et al. |
| 6,269,819 | B1 * | 8/2001 | Oz et al. ........................ 128/898 |
| 6,299,637 | B1 | 10/2001 | Shaolian et al. |
| 6,454,777 | B1 | 9/2002 | Green |
| 6,458,153 | B1 | 10/2002 | Bailey et al. |
| 6,506,339 | B1 | 1/2003 | Girardot et al. |
| 6,517,553 | B2 | 2/2003 | Klein et al. |
| 6,540,782 | B1 | 4/2003 | Snyders |
| 6,551,331 | B2 | 4/2003 | Nobles et al. |
| 6,558,418 | B2 | 5/2003 | Carpentier et al. |
| 6,562,052 | B2 | 5/2003 | Nobles et al. |
| 6,572,652 | B2 | 6/2003 | Shaknovich |
| 6,726,717 | B2 | 4/2004 | Alfieri et al. |
| 6,730,118 | B2 | 5/2004 | Spenser et al. |
| 6,733,509 | B2 | 5/2004 | Nobles et al. |
| 6,749,630 | B2 | 6/2004 | McCarthy et al. |
| 6,769,434 | B2 | 8/2004 | Liddicoat et al. |
| 6,821,297 | B2 | 11/2004 | Snyders |
| 6,858,039 | B2 | 2/2005 | McCarthy |
| 6,893,460 | B2 | 5/2005 | Spenser et al. |
| 6,899,704 | B2 | 5/2005 | Sterman et al. |
| 6,908,481 | B2 | 6/2005 | Cribier |
| 6,911,034 | B2 | 6/2005 | Nobles et al. |
| 7,004,952 | B2 | 2/2006 | Nobles et al. |
| 7,078,163 | B2 | 7/2006 | Torrianni |
| 7,090,686 | B2 | 8/2006 | Nobles et al. |
| 7,100,614 | B2 | 9/2006 | Stevens et al. |
| 7,377,926 | B2 | 5/2008 | Topper et al. |
| 7,510,572 | B2 | 3/2009 | Gabbay |
| 7,803,185 | B2 * | 9/2010 | Gabbay ........................ 623/2.11 |
| 7,905,892 | B2 | 3/2011 | Nobles et al. |
| 2001/0002445 | A1 * | 5/2001 | Vesely ........................ 623/2.11 |
| 2001/0020181 | A1 | 9/2001 | Layne |
| 2001/0021872 | A1 | 9/2001 | Bailey et al. |
| 2002/0042651 | A1 | 4/2002 | Liddicoat et al. |
| 2002/0165571 | A1 | 11/2002 | Herbert et al. |
| 2003/0109924 | A1 | 6/2003 | Cribier |
| 2005/0043791 | A1 | 2/2005 | McCarthy et al. |
| 2005/0049698 | A1 | 3/2005 | Bolling et al. |
| 2005/0131533 | A1 | 6/2005 | Alfieri et al. |
| 2005/0228407 | A1 | 10/2005 | Nobles et al. |
| 2005/0251251 | A1 | 11/2005 | Cribier |
| 2006/0195120 | A1 | 8/2006 | Nobles et al. |
| 2007/0043385 | A1 | 2/2007 | Nobles et al. |
| 2007/0276413 | A1 | 11/2007 | Nobles et al. |
| 2007/0276414 | A1 | 11/2007 | Nobles et al. |

FOREIGN PATENT DOCUMENTS

| | | |
|---|---|---|
| EP | 0941698 | 5/2005 |
| EP | 1570790 | 11/2008 |
| WO | WO 9933414 A1 | 7/1999 |

* cited by examiner

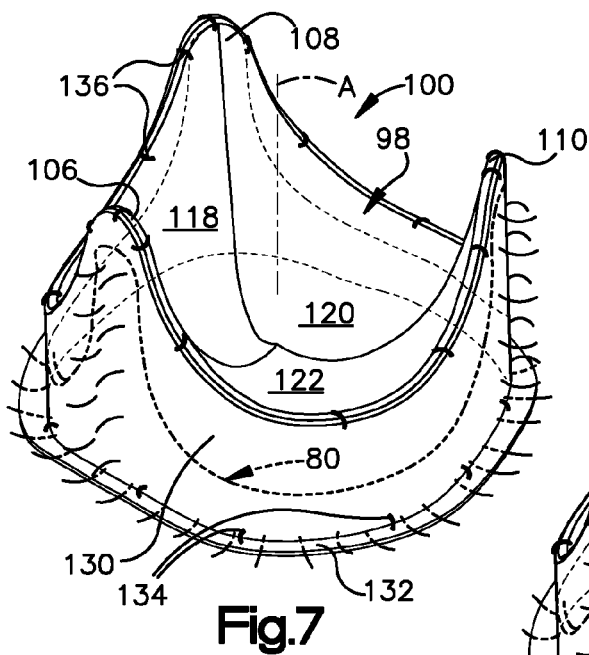
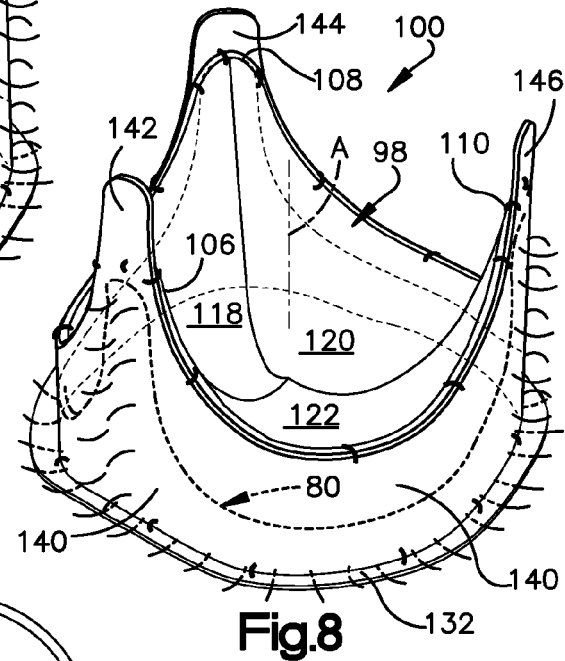
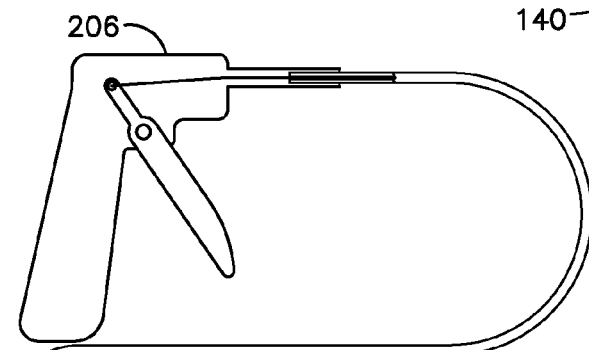
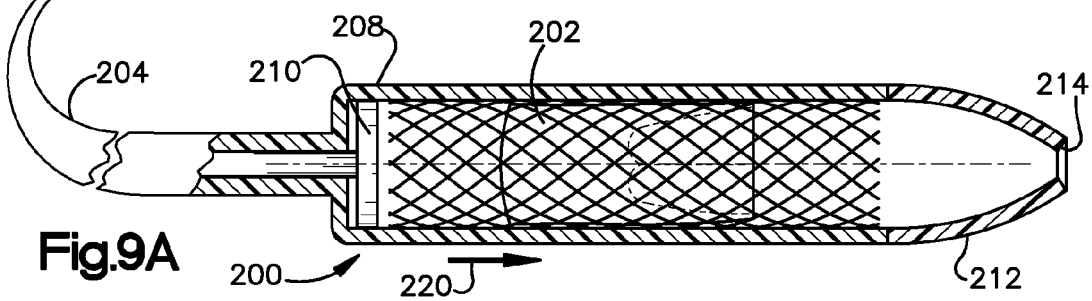
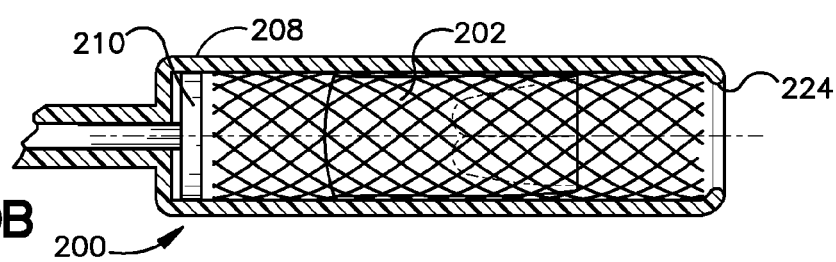

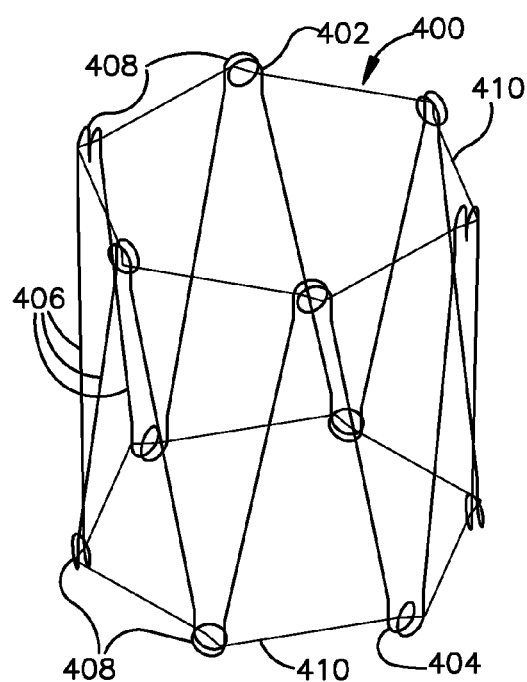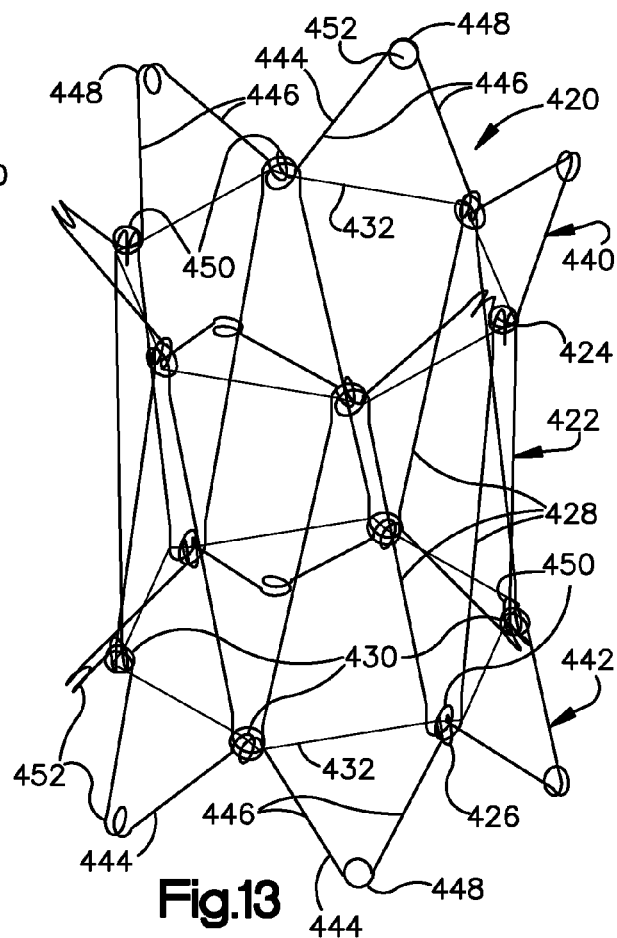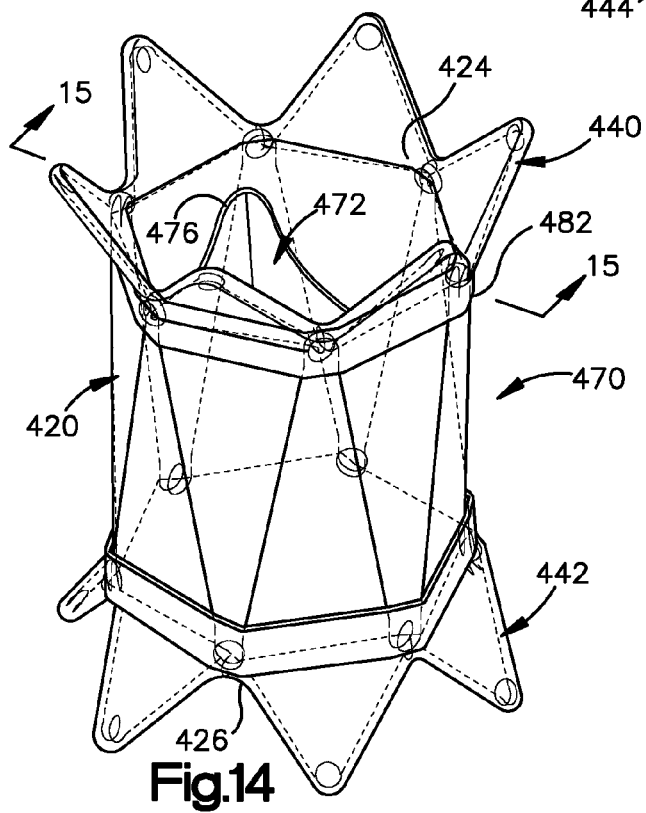

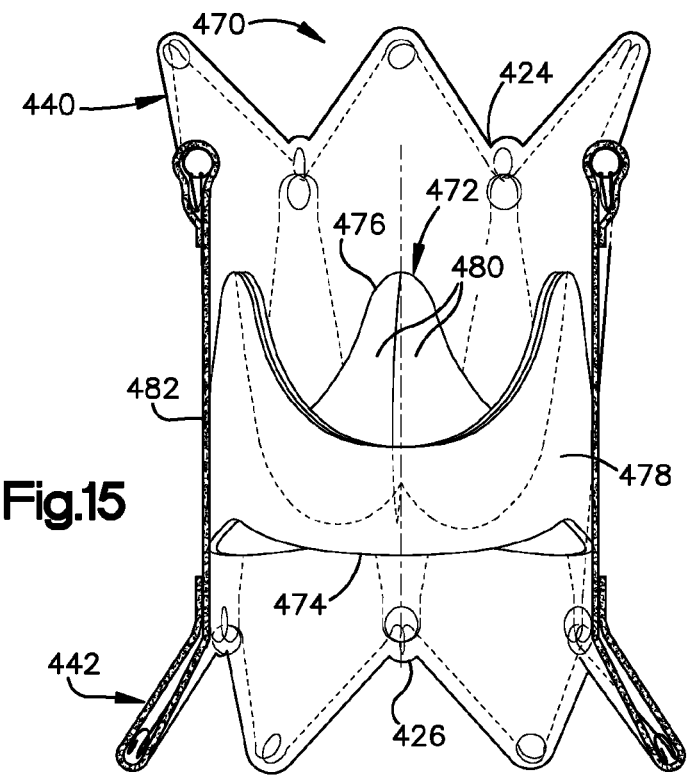
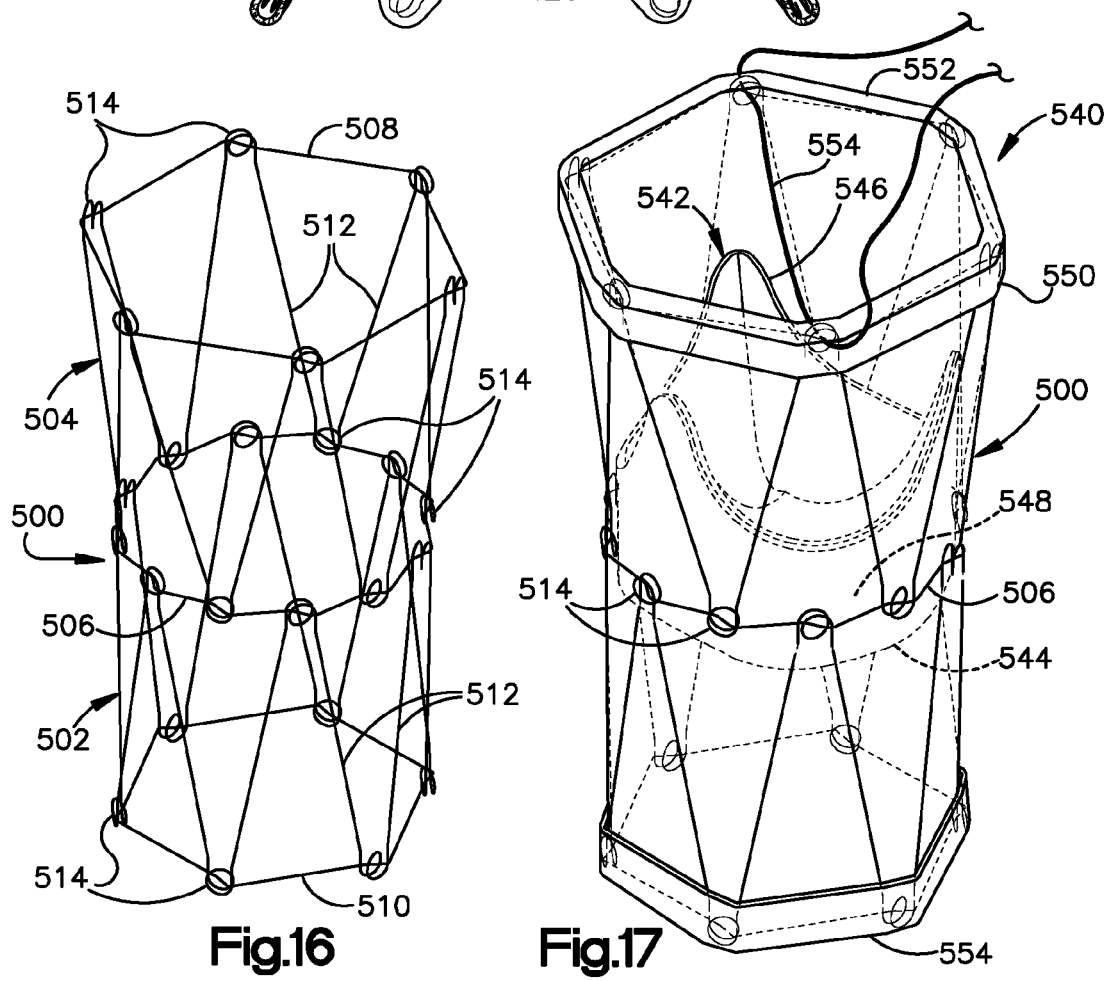

US 9,414,912 B2

METHOD FOR DIRECT IMPLANTATION OF A HEART VALVE PROSTHESIS

REFERENCE TO RELATED APPLICATIONS

This application is a continuation of U.S. patent application Ser. No. 12/482,781, now which was filed Jun. 11, 2009, and entitled INJECTABLE HEART VALVE PROSTHESIS FOR LOW-INVASIVE IMPLANTATION, which is a continuation of U.S. patent application Ser. No. 10/266,380, now U.S. Pat. No. 7,803,185, which was filed Oct. 8, 2002, and entitled HEART VALVE PROSTHESIS AND SUTURELESS IMPLANTATION OF A HEART VALVE PROSTHESIS, which is a continuation-in-part of U.S. patent application Ser. No. 09/973,609, now U.S. Pat. No. 7,510,572, which was filed on Oct. 9, 2001, and entitled HEART VALVE PROSTHESIS AND SUTURELESS IMPLANTATION OF A HEART VALVE PROSTHESIS, which is a continuation-in-part of U.S. patent application Ser. No. 09/659,882, which was filed on Sep. 12, 2000, and entitled VALVULAR PROSTHESIS AND METHOD OF USING SAME. Each of the above-identified applications is incorporated herein by reference in its entirety.

TECHNICAL FIELD

The invention relates to a method for direct implantation of a heart valve prosthesis.

BACKGROUND

It is well known to utilize mechanical heart valves, such as the ball check valve, and natural tissue cardiac valves to replace defective aortic and mitral valves in human patients. One type of natural tissue heart valve typically employs a porcine valve for implantation in a human, as they are very similar to human valves of appropriate size and generally are easy to procure. Typically, the porcine valve is fixed by chemically treating it, such as with an appropriate glutaraldehyde solution. The treated porcine valve further may be mounted into a stent to support the valve at a fixed position.

A stent typically is formed of a resilient material, such as a plastic (e.g., DELRIN). Examples of various stent structures are disclosed in U.S. Pat. Nos. 3,983,581, 4,035,849. The stent usually is covered with a fabric material, such as DACRON or a suitable textile material. The fabric material provides structure for securing the valve relative to the stent. The stented heart valve prosthesis may be implanted into a patient for a heart valve replacement.

In order to surgically implant a heart valve into a patient, the patient typically is placed on cardiopulmonary bypass during a complicated, but common, open chest procedure. In certain situations, an individual requiring a heart valve replacement may be sufficiently ill, such that placing the individual on cardiopulmonary bypass may pose too great of risk. Such individuals may correspond to a class of patients who may have a non-functioning pulmonary valve or severe aortic valve insufficiency. In particular, many older patients having a deficient aortic or pulmonic valve may be too ill to survive conventional open-heart surgery.

Patients exhibiting these and other conditions would benefit from an improved heart valve prosthesis that may be implanted by a less invasive and/or more efficient implantation procedure.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The invention relates to a method for direct implantation of a heart valve prosthesis.

One aspect of the invention provides method for implanting a heart valve into a patient's heart. The method can include compressing the heart valve to a reduced diameter and mounting the heart valve having the reduced diameter within an implanter. An opening is created in tissue of the patient's heart at a location through which the implanter is to be inserted and provide a path to a target implantation location. The implanter is advanced through the opening to position the heart valve at a desired target location in the patient's heart, and the heart valve is deployed from the implanter at the target location to implant the heart valve. The method can be used for direct implantation of the prosthesis apically or through a vessel such as the aorta.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which:

FIG. 7 is an example of a valvular prosthesis, illustrating an outer sheath over the prosthesis of FIG. 6B in accordance with the present invention.

FIG. 8 is another example of a valvular prosthesis, illustrating an outer sheath over the prosthesis of FIG. 6B in accordance with the present invention.

FIG. 9A is an example of enclosure that may be utilized for implanting a valvular prosthesis in accordance with the present invention.

FIG. 9B is an example of another enclosure catheter mechanism that may be utilized for implanting a valvular prosthesis in accordance with the present invention.

FIG. 12 is an example of a support structure in accordance with an aspect of the present invention.

FIG. 13 is an example of another support structure in accordance with an aspect of the present invention.

FIG. 14 is an example of a heart valve prosthesis employing the support structure in accordance with an aspect of the present invention.

FIG. 15 is a cross-sectional view of a heart valve prosthesis taken along line 15-15 in FIG. 14.

FIG. 16 is an example of another type of support structure in accordance with an aspect of the present invention.

FIG. 17 is another example of a heart valve prosthesis employing the support structure of FIG. 16 in accordance with an aspect of the present invention.

DESCRIPTION OF THE INVENTION

Figure 1A:
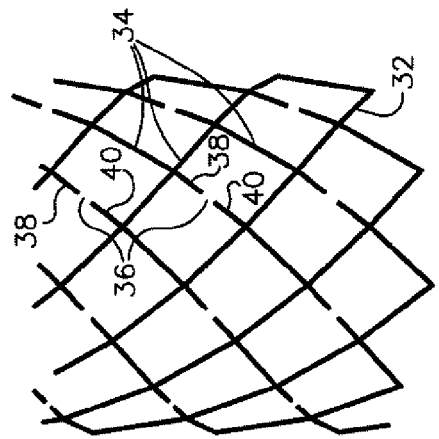
FIG. 1A is an enlarged view of part of the stent of FIG. 1 in a first condition.
Figure 1B:
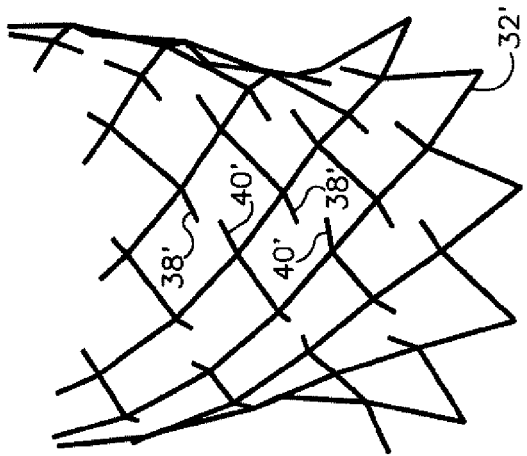
FIG. 1B is an enlarged view of part of the stent of FIG. 1, similar to FIG. 1A, illustrating the part of the stent in a second condition.
Figure 2:
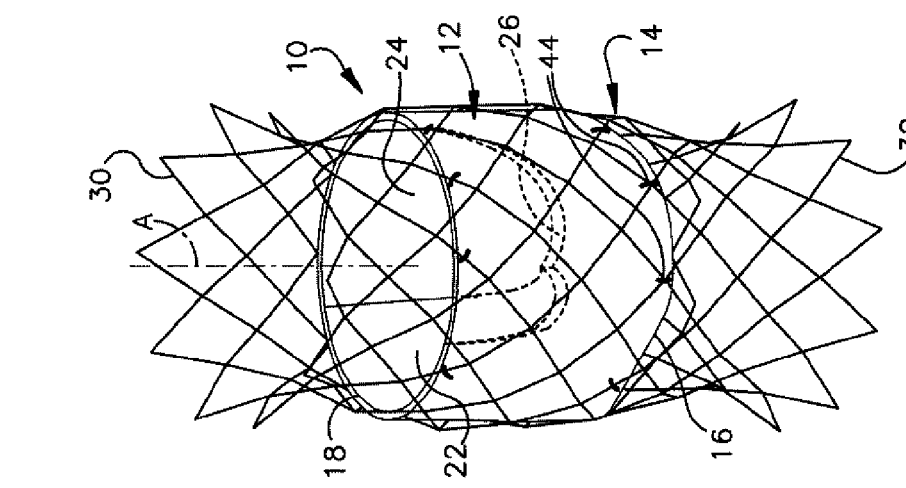
FIG. 2 is an example of a valvular prosthesis in accordance with the present invention.
Figure 1:
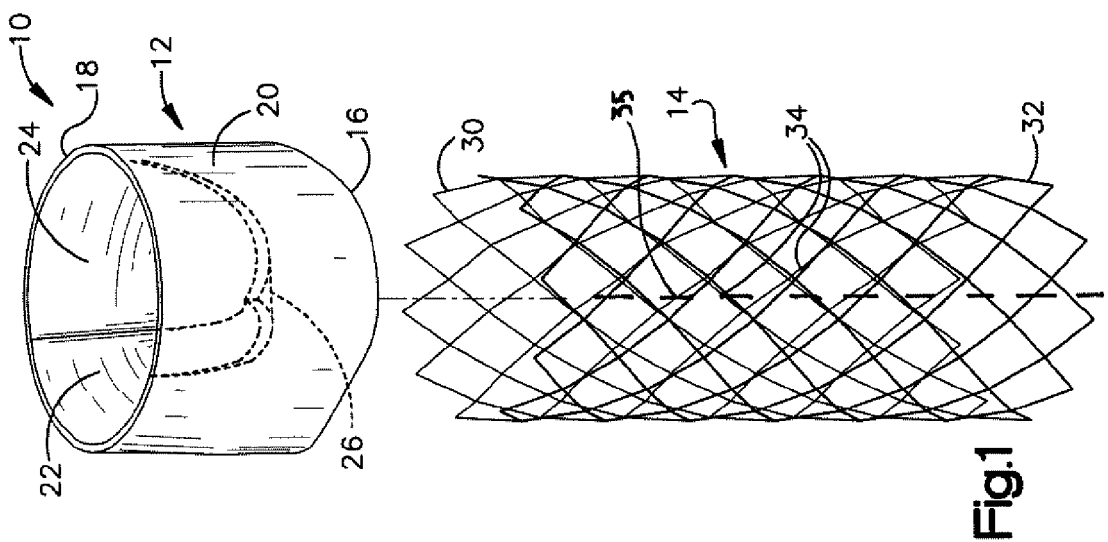
FIG. 1 is an exploded isometric view of a valve and stent apparatus that may be utilized to form a prosthesis in accordance with the present invention.

FIG. 1 is an exploded view of a valvular prosthesis 10 in accordance with an aspect of the present invention. The prosthesis 10 includes a valve portion 12 and a stent portion 14 that may be assembled to form the valvular prosthesis 10, such as shown in FIG. 2.

The valve portion 12 includes inflow and outflow ends 16 and 18 spaced apart from each other by a length of a generally cylindrical sidewall portion 20. While the inflow and outflow ends 16 and 18 are illustrated as being annular in FIGS. 1 and 2, those skilled in the art will understand and appreciate that other configurations (e.g., generally sinusoidal ends) also could be used in accordance with the present invention.

The valve portion 12 also includes one or more leaflets 22, 24, and 26 that are attached to and extend from an interior of the sidewall portion 20. In the example illustrated in FIGS. 1 and 2, the valve portion 12 includes three leaflets 22, 24 and 26, although other numbers of leaflets, such as a single leaflet or two leaflets, also could be used.

The valve portion 12 may be formed of any substantially biocompatible valve apparatus. By way of example, the valve portion 12 may include an animal heart valve (e.g., pulmonic or aortic), a manufactured valve device (e.g., a valve as shown and described in U.S. Pat. Nos. 4,759,758 or 5,935,163) a venous valve (e.g., a bovine or equine jugular venous valve). Those skilled in the art will understand and appreciate that the foregoing list is not intended to be exhaustive but, instead, is intended illustrate a few examples of the types of valves that may be utilized in a valvular prosthesis 10 in accordance with an aspect of the present invention.

If the valve portion 12 is formed of a natural tissue material, such as an animal heart valve, a venous valve, or a composite valve manufactured of natural tissue, the valve should be chemically fixed, such as in a suitable solution of glutaraldehyde in a closed condition (as is known in the art). The fixation process facilitates closure of the valve 12 under application of back flow pressure, while remaining open during normal forward blood flow through the valve 12. By way of example, the natural tissue valve may be cross-linked with glutaraldehyde and undergo a detoxification process with heparin bonding. The treatment improves biocompatibility of the valve apparatus 12 and mitigates calcification and thrombus formation.

In accordance with an aspect of the present invention, the valve portion 12 exhibits structural memory. That is, if the valve apparatus 12 is compressed, such as to a reduced diameter at the time of being implanted, it will return substantially to its original shape and configuration upon removal of radially inward forces. As a result, the valve apparatus 12 is able to maintain coaptation of the leaflets 22, 24, and 26 even after being deformed. The memory feature of the valve is further improved by mounting it within the stent portion 14.

Turning now to the stent portion 14, such as shown in FIGS. 1 and 2, the stent includes an inflow end 30 and an outflow end 32. In this example, the inflow and outflow ends 30 and 32 are spaced apart from each other a distance that is greater than the distance between the corresponding ends 18 and 16 of the valve 12. In this way, the ends of the stent 30 and 32 may extend beyond the respective ends 18 and 16 of the valve 12 (e.g., by about a few millimeters), such as shown in FIG. 2. The stent portion 14 also may include outwardly turned portions at the inflow and outflow ends 30 and 32 of the stent, which, when implanted, may engage and/or be urged into the surrounding tissue to mitigate movement thereof.

According to an aspect of the present invention, the stent 14 may deformable between first and second conditions, in which the first condition has a reduced cross-sectional dimension relative to the second condition. FIGS. 1 and 2 illustrate the stent portion 14 as being formed of a mesh or weave 34 extending between the ends 30 and 32. The mesh 34 may be a metal, an alloy, or other suitable material that may help support a valve mounted therein and/or help anchor the valve at a desired position when implanted.

By way of example, the mesh may be formed of a shape memory alloy material, such as may be formed of a nitinol (nickel-titanium alloy) wire. Shape memory (or thermal memory) is a characteristic in which a deformed part remembers and recovers to a pre-deformed shape upon heating. By forming the stent 14 of a shape memory alloy, the stent is inelastically deformable to new shape, such as a reduced cross-sectional dimension, when in its low-temperature (martensitic) form. For example, the stented valve (FIG. 2) may be cooled, such as by being introduced to a cooling solution (e.g., water), and then compressed.

When the stent 14 is heated to its transformation temperature, which may vary according to the alloy composition, it quickly reverts to its high-temperature (austenitic) form. The stented valve may retain the compressed condition by keeping it cooled. Alternatively, the stent and valve may be retained in the compressed position, such as with sutures circumscribing the structure, a cylindrical enclosure around the structure, etc. The prosthesis 10 will then return toward its high-temperature (or original) position upon removal of the retaining element.

It is to be appreciated that, alternatively, the stent 14, in accordance with an aspect of the present invention, could be inelastically deformable so as to require an intervening force to return the deformed stent substantially to a desired configuration. For example, a balloon catheter or spring mechanism (schematically indicated by dashed line at 35) could be employed to urge the stent and the valve located therein generally radially outward so that, after being implanted to a desired position, the stent will engage the surrounding tissue in a manner to inhibit movement relative to the surrounding tissue.

FIGS. 1A and 1B illustrate an enlarged view of part of the stent 14 in accordance with an aspect of the present invention. In this example, some strands of the mesh 34 are broken to define spaces 36 between adjacent lateral extensions or spike portions 38 and 40. As the stent 14 is deformed, such as shown in FIG. 1B, the spike portions 38' and 40' may extend radially outwardly from the stent in different directions. In addition, the inflow end 32' also may flare outwardly for engagement with surrounding tissue when implanted. For example, some spikes 40, 40' may extend generally outwardly and toward an outflow end of the stent 14, while others 38, 38' may extend generally outwardly and toward an inflow end 32, 32'. The spikes thus are operable to engage tissue, when implanted, so as to inhibit axial movement of the stent 14 relative to the surrounding tissue.

Referring back to FIG. 2, the valve portion 12 is disposed generally coaxially within the cylindrical stent portion 14 relative to the central axis A. The valve 12 may be affixed relative to the stent portion 14, such as by one or more sutures 44. The sutures 44 may be located at the inflow and outflow ends 16 and 18 of the valve 12 to connect the valve to the stent 14 to inhibit axial movement of the valve relative to the stent. Alternatively or additionally, axial movement between the stent 14 and valve 12 may be mitigated due to friction fitting between the stent and valve portion. For example, as illustrated in FIG. 2, the valve portion 12 has a cross-sectional diameter that is slightly larger than that of the stent 14, such that the prosthesis 10 bulges somewhat in the middle and is narrower near the inflow and outflows ends 16 and 18 of the valve portion 12.

As mentioned above, the stent portion 14 may be formed of a shape memory alloy. In this way, the valvular prosthesis 10 may be compressed to a reduced cross-sectional dimension about the axis A and maintained at the reduced dimension while being implanted. Once the valvular prosthesis 10 is at a desired implantation position, the prosthesis may be permitted to return toward its original cross-sectional dimension so as to engage a valve wall or other surrounding tissue at the desired position. The engagement between the stented valvular prosthesis 10 and the surrounding tissue inhibits axial movement of the prosthesis relative to the tissue. In accordance with an aspect of the present invention, lateral extensions or spikes (see, e.g., FIGS. 1A and 1B) may extend outwardly from the stent to further inhibit axial movement. Those skilled in the art will understand and appreciate that a valvular prosthesis 10, in accordance with the present invention, may be utilized to replace a heart valve or utilized as an intravascular implant to provide an operable venous valve.

Figure 3:
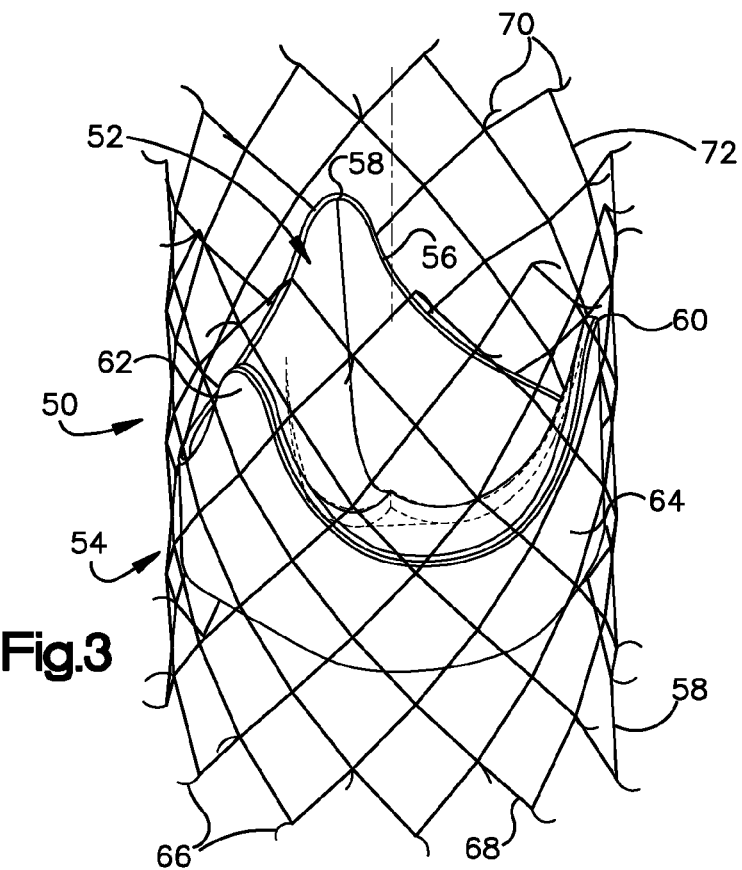
FIG. 3 is another example of valvular prostheses in accordance with the present invention.

FIG. 3 illustrates another example of a stented valvular prosthesis 50 in accordance with an aspect of the present invention. The prosthesis 50 in this example includes a valve portion 52 mounted within a stent portion 54. The valve portion 52 in this example, has a generally sinusoidal outflow end 56 having a plurality of commissure posts 58, 60, and 62 extending from an annular base portion 64, with corresponding sinuses located between each adjacent pair of posts. It is to be appreciated that, alternatively, a valve having a sidewall portion according to generally cylindrical configuration of FIGS. 1 and 2 also could be used in conjunction with the stent portion 54.

The stent portion 54 in this example is formed of a deformable mesh, which may be substantially identical to that described above with respect to FIGS. 1-2. The stent portion 54 also includes a plurality of spikes extending generally radially outwardly from the stent portion. In particular, one set of spikes 66 extend from an inflow end 68 of the stent portion 54 and another set of spikes 70 extend from an outflow end 72 of the stent.

Figure 4:
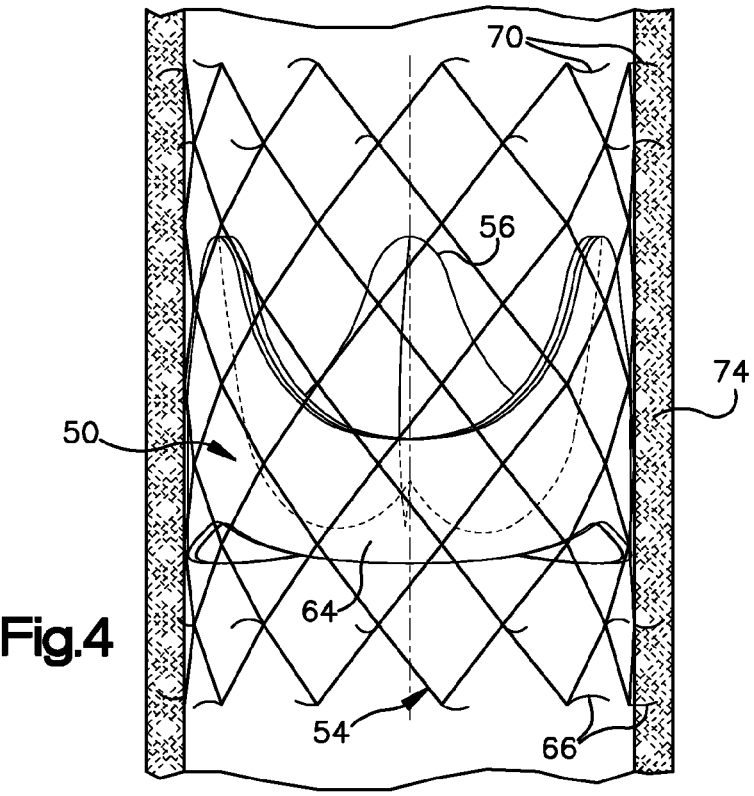
FIG. 4 is an example of the valvular prostheses of FIG. 3 implanted within a tubular member in accordance with the present invention.

FIG. 4 illustrates the prosthesis 50 of FIG. 3 mounted in an expanded condition within a generally cylindrical sidewall 74. The sidewall 74, for example, may be a venous valve wall, a pulmonary artery, an aorta, etc. In this example, the spikes 66 and 70 engage and/or extend into the valvular wall 74 to inhibit axial movement of the prosthesis 50 relative to the valve wall 74.

Figure 5:
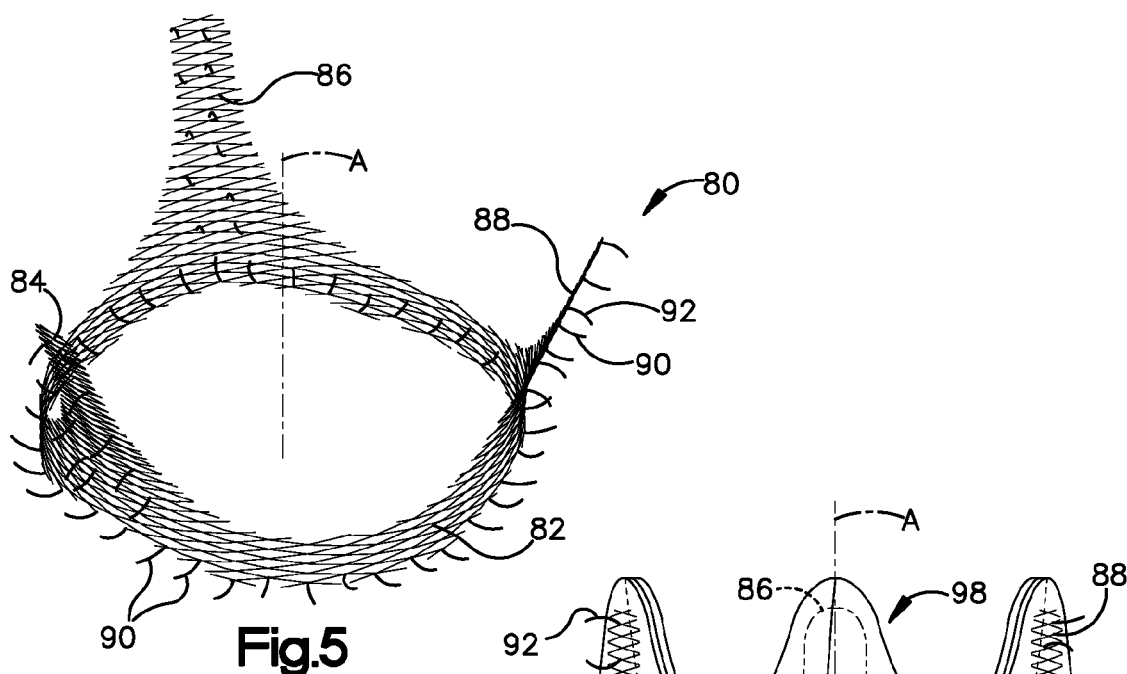
FIG. 5 is another example of a stent apparatus in accordance with the present invention.

FIG. 5 illustrates another example of a stent apparatus 80 which may be utilized as part of a valvular prosthesis in accordance with an aspect of the present invention. The stent 80 includes a generally annular base portion 82 and a plurality of axially extending portions (or stent posts) 84, 86 and 88 extending generally axially from the base portion. The post portions 84, 86 and 88 are circumferentially spaced apart for generally radial alignment with corresponding commissure posts of an associated valve wall. While the example of the stent 80 in FIG. 5 has three stent posts 84, 86 and 88, those skilled in the art will understand and appreciate that other numbers of posts also could be utilized in accordance with an aspect of the present invention. Typically, however, the number of posts and their relative circumferential position correspond to the number of leaflets of a valve to be mounted within the stent 80.

In accordance with an aspect of the present invention, each of the stent posts 84, 86, 88 may extend radially outwardly an angle Θ relative to the axis A. By way of example, the angle Θ may range from about 10 to about 60 degrees relative to a line drawn through the juncture of each post and the base 82 parallel to the central axis A. The outwardly extending posts 84, 86, and 88 facilitate engagement between each respective post and surrounding tissue when implanted, as the posts (being resilient) tend to urge radially outwardly and into engagement with such tissue.

The stent 80 also includes a plurality of spikes 90 and 92 that extend radially outwardly from the stent. In particular, some outwardly extending spikes 90 are curved generally toward an outflow end of the stent and others 92 are curved generally toward an inflow end of the stent. In addition, a row of spikes 90 may extend outwardly relative to the stent 80 at the inflow end thereof, which spikes also are curved generally toward the outflow end. The varying contour of the spikes 90 and 92 mitigates axial movement of the stent 80 (in both axial directions) relative to tissue engaged thereby, such as after being implanted. It is to be understood and appreciated that, while a single row of spikes is illustrated near the inflow end of the stent in FIG. 5, two or more axially spaced apart rows of spikes extending generally radially outwardly from the stent 80 could also be utilized in accordance with an aspect of the present invention. The rows of spikes may be curved toward each other to provide a clamping function on surrounding tissue when implanted.

Figure 6A:
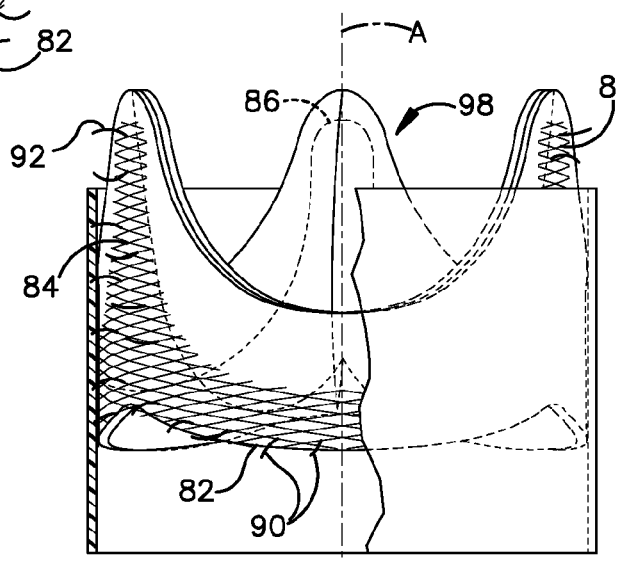
FIG. 6A is an example of the stent of FIG. 5 mounted within an enclosure in accordance with the present invention.

FIG. 6A illustrates the stent of FIG. 5 mounted within a tubular structure 94 that has an inner diameter that is substantially commensurate with the outer diameter of the base portion 82 of the stent 80. The tubular structure 94 may be formed of a plastic or other material effective to hold the stent posts 84, 86, and 88 at a radial inward position. In this way, the tubular structure 94 urges the stent posts 84, 86, and 88 radially inward to a position that facilitates mounting a valve 98 therein. For example, the valve 98 may be positioned within and connected to the stent 80, such as by sutures applied along the base portion 82 and the stent posts 84, 86, and 88; without having to manually hold each of the posts against corresponding parts of the valve.

Figure 6B:
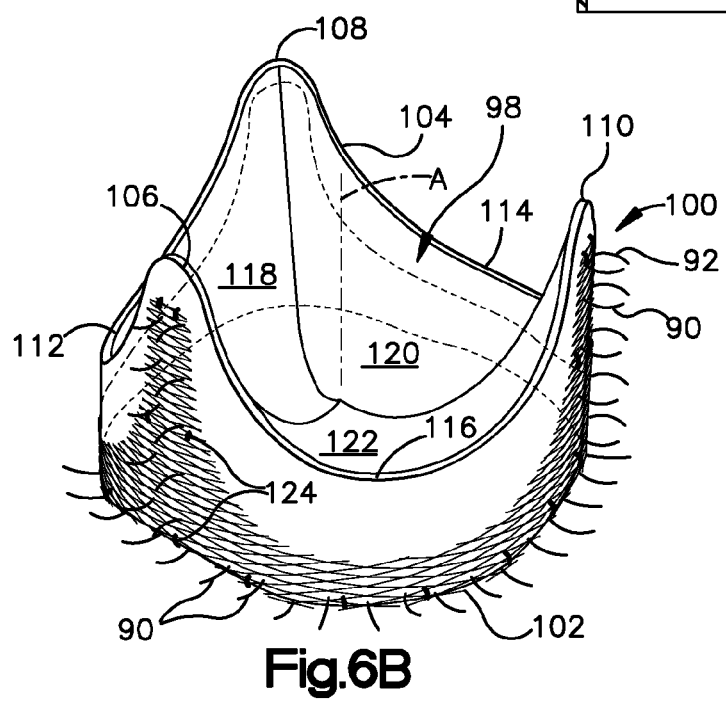
FIG. 6B is an example of valvular prostheses having the stent of FIG. 5 mounted therein in accordance with the present invention.

FIG. 6B illustrates an example in which a valve 98 has been mounted within the stent 80 of FIG. 5 to form a valvular prosthesis 100. The valve 98 includes an inflow end 102 and an outflow end 104. The inflow end 102 of the valve 98 is positioned adjacent relative to the inflow end of the stent 80. The outflow end 104 of the valve 98 is contoured to include axially extending commissure posts 106, 108 and 110 with sinuses 112, 114 and 116 located between each adjacent pair of posts. Valve leaflets 118, 120 and 122 extend between adjacent posts commensurate with the location of each of the sinuses 112, 114 and 116. The stent 80 may be connected to the valve 98 via sutures 124.

In accordance with an aspect of the present invention, the prosthesis 100 of FIG. 6B is a stented valve, which may be covered with an outer sheath of a substantially biocompatible material.

FIG. 7 illustrates an example of a valvular prosthesis in which an outer sheath 130 has been applied over the stent 80 and at least part of the exposed exterior portion of the valve 98 in accordance with an aspect of the present invention. As illustrated, the outer sheath 130 may have inflow and outflow ends having generally the same contour as the sidewall of the valve 98 and the stent 80. The outer sheath 130 may be a sheath of natural tissue pericardium (e.g., bovine, equine, porcine, etc.), another biological tissue material (e.g., collagen), or a synthetic material (e.g., Dacron). When a biological tissue is utilized, for example, it may be cross-linked with glutaraldehyde and detoxified with heparin bonding.

An implantation flange (or sewing ring) 132 may be formed at the inflow end of the prosthesis 100. The implantation flange 132 may be formed of substantially the same material as the outer sheath 140, such as formed from the outer sheath 130 or by attaching a separate flange by other methods. The outer sheath 130 may be attached to the valve 98 and/or to the stent 80 by applying sutures 134 and 136 at the respective inflow and outflow ends of the prosthesis 100. Some of the spikes 90, 92 may extend through the outer sheath 130 so as to mitigate axial movement of the prosthesis 100 relative to surrounding tissue when the prosthesis is implanted. Sutures 134 and 136 may be applied respectively at the inflow and outflow ends to secure the outer sheath relative to the stent 80 and the valve 100. The outer sheath 130 may include an outflow end that conforms to the contour of the outflow end 104 of the valve 100.

FIG. 8 illustrates another example of valvular prosthesis 100 that is similar to that shown and described in FIG. 7, in which identical reference numbers refer to corresponding parts previously identified herein. The prosthesis 100 includes having an outer sheath 140 that is disposed about the stent 80 and the valve 98 and having an outflow end that follows the contour of the prosthesis 100 (e.g., generally sinusoidal. In addition, the outer sheath 140 includes a plurality of axially extending lobes 142, 144 and 146 extending axially beyond the outflow attachment of the valve leaflets 118, 120, and 122. In this example, the lobes 142, 144 and 146 extend axially a length beyond the commissure posts 106, 108 and 110 of the valve 98. The axially extending lobes 142, 144 and 146 provide additional structure that may be utilized to help secure the prosthesis 100 relative to surrounding tissue when being implanted. When the prosthesis 100 of FIG. 8 is implanted, for example, sutures may be applied through the lobes 142, 144 and 146 to help secure the commissure posts of the prosthesis relative to the surrounding tissue. Additional sutures also could be applied at the inflow end to the implantation flange 132 located thereat.

FIGS. 9A and 9B illustrate variations of an implantation apparatus 200 that may be utilized to implant a valvular prosthesis 202 in accordance with an aspect of the present invention. It is to be understood and appreciated that any of the prosthesis shown and/or described herein may be implanted with such an implantation apparatus.

With reference to FIG. 9A, by way of example, the implantation apparatus 200 may be in the form of a catheter system. The implantation apparatus includes an elongated connecting element 204 extending between a trigger mechanism 206 and an enclosure 208, in which the prosthesis 202 is located. At least a portion of the prosthesis 202 is located within the enclosure 208. A plunger mechanism 210 is located at a proximal end of the enclosure 208 for urging the prosthesis 202 generally axially from the enclosure 208. An opposite end 212 of the enclosure 208 may be formed of a pliable material or a plurality of moveable members that may open as the prosthesis 202 is urged through an opening 214 located at a distal end. It is to be appreciated that the length of the connecting element 204 may vary according to where the valvular prosthesis 202 is to be implanted and the method of implantation.

The valvular prosthesis 202 is illustrated within the enclosure 208 in a compressed condition, such as described above. That is, the valvular prosthesis 202 within the enclosure 208 has a cross-sectional dimension that is less than its normal cross-sectional dimension, being maintained in such position by the enclosure. Those skilled in the art will appreciate that the orientation of the valvular prosthesis 202 will vary depending upon the direction in which blood is to flow through the valve when implanted.

By way of example, the external stent of the valvular prosthesis 202 may be formed of a deformable material, such as a shape memory alloy material (e.g., nitinol), which maintains its shape when cooled. Accordingly, the prosthesis 202 may be cooled (e.g., within a suitable fluid), compressed to a desired reduced cross-sectional dimension so as to fit within the enclosure 208, and then inserted within the enclosure. The prosthesis 202, after the stent being heated (e.g. to an ambient temperature), may desire to expand to its original dimension and configuration. However, the enclosure 208 or another retaining mechanism, such as a suture or other tubular member around the prosthesis, may be used to restrict its expansion. The compression of the valvular prosthesis 202 may be performed just prior to surgery to mitigate undesired permanent deformation of the valvular prosthesis 202. The plunger mechanism may be urged in the direction of arrow 220, such as by activating the trigger 206. Movement of the plunger 210, in turn, causes the prosthesis 202 to also be moved in the direction of the arrow 220. As the prosthesis 202 is urged through the opening 214 and discharged therefrom, the prosthesis may expand. Accordingly, the opening 214 should be positioned at the location where the prosthesis 202 is to be implanted prior to discharge. When the prosthesis 202 expands toward its original condition, the sidewall of the stent and/or spikes associated with the stent may engage and/or be urged into surrounding tissue so as to mitigate axial movement of the prosthesis relative to the surrounding tissue. As a result, the prosthesis may be implanted without sutures to provide an operable valve, such as a heart valve or a venous valve. When a valvular prosthesis is being employed as a heart valve, in accordance with present invention, it will be appreciated that the prosthesis may be implanted either as part of an open chest procedure or the patient's chest may be closed. Additionally, other expandable stent structures also could be utilized in accordance with an aspect of the present invention.

FIG. 9B illustrates another example of an enclosure 208 which may be utilized, in accordance with an aspect of the present invention, to implant a prosthesis 202. The enclosure 208 has an opening 224 at its distal end through which the prosthesis 202 may be discharged. In this example, the opening 224 is about the same diameter as the enclosure itself, although it may be curved slightly inwardly at the distal end thereof. This facilitates discharge of the prosthesis 202 without having an expandable distal end portion, such as shown and described with respect to FIG. 9A.

Figure 10:
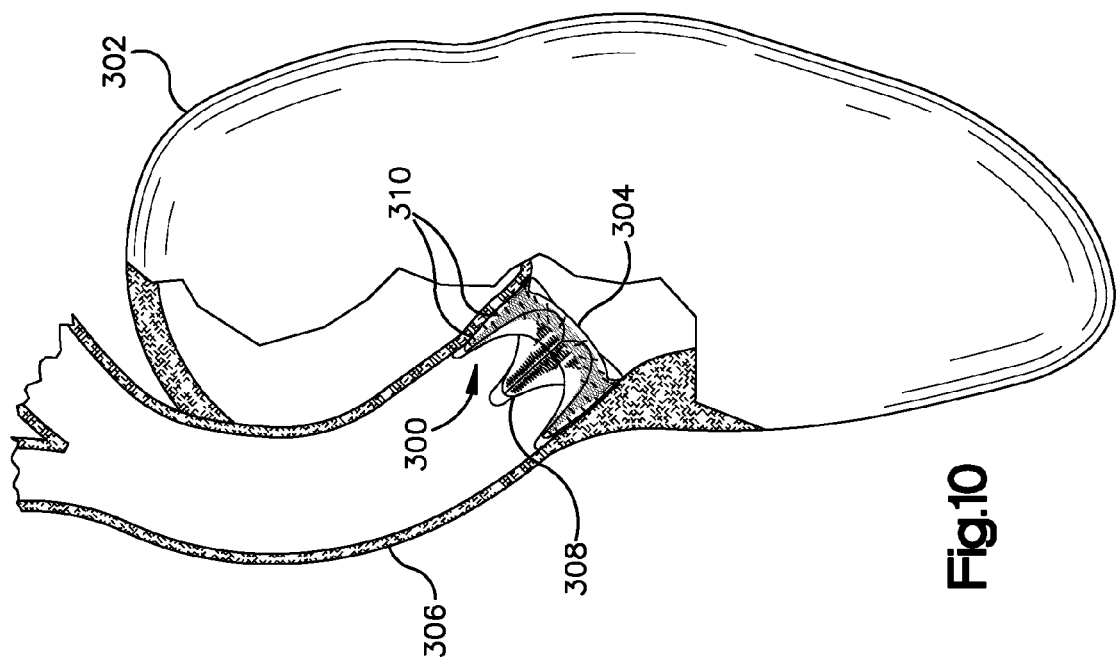
FIG. 10 is an example of a valvular prostheses implanted in an aortic position of a heart in accordance with the present invention.

FIG. 10 illustrates an example of a valvular prosthesis 300 implanted in a heart 302 in an aortic position. When being implanted at an aortic position, an aortic valve (e.g., equine, porcine, bovine, etc.) may be utilized for the valve portion of the prosthesis, although other types of valve portions also could be used. Prior to implanting the prosthesis 300, the aortic valve or at least calcified portions thereof should be removed. An inflow end 304 of the prosthesis 300 is annularized with respect to the annulus of the aorta 306. An outflow portion 308 of the prosthesis 300 extends axially into the aorta 306, with the stent posts engaging the interior of the aortic wall. As mentioned above, a plurality of spikes 310 may extend laterally from the stent portion of the valvular prosthesis 300 to engage the aorta 306 to help maintain a desired axial orientation of the valvular prosthesis relative to the aorta 306.

The valvular prosthesis 300 may be implanted in a compressed condition. It is to be appreciated that the valvular prosthesis 300 may be implanted in the aortic position during a conventional open chest procedure or during a closed chest procedure. The valvular prosthesis 300 may be implanted by using a catheter (or other structure) to retain the prosthesis in a compressed condition. The catheter may then be used to position the valve at a desired position, such as by utilizing a suitable imaging technology (e.g., x-ray, ultrasound, or other tomography device) or a direct line of sight. Once at the desired position, the prosthesis 300 may be discharged from its retaining mechanism (e.g., an enclosure) so that it expands toward its original expanded configuration at the desired position within the aorta 306.

It is to be understood and appreciated, though, if the patient has a calcified aortic valve, the patient typically must be put on cardiopulmonary bypass to remove the calcium and implant the valve. Advantageously, a valvular prosthesis 300 in accordance with the present invention may be implanted more efficiently so as to mitigate morbidity and mortality of the patient. In addition, the prosthesis may be implanted without sutures or, alternatively, some sutures may be utilized. For example, sutures may be applied at the inflow end 304 (e.g., at a sewing ring) and/or at the outflow end 308, such as when the prosthesis is configured to have axially extending lobes (see FIG. 8).

Figure 11:
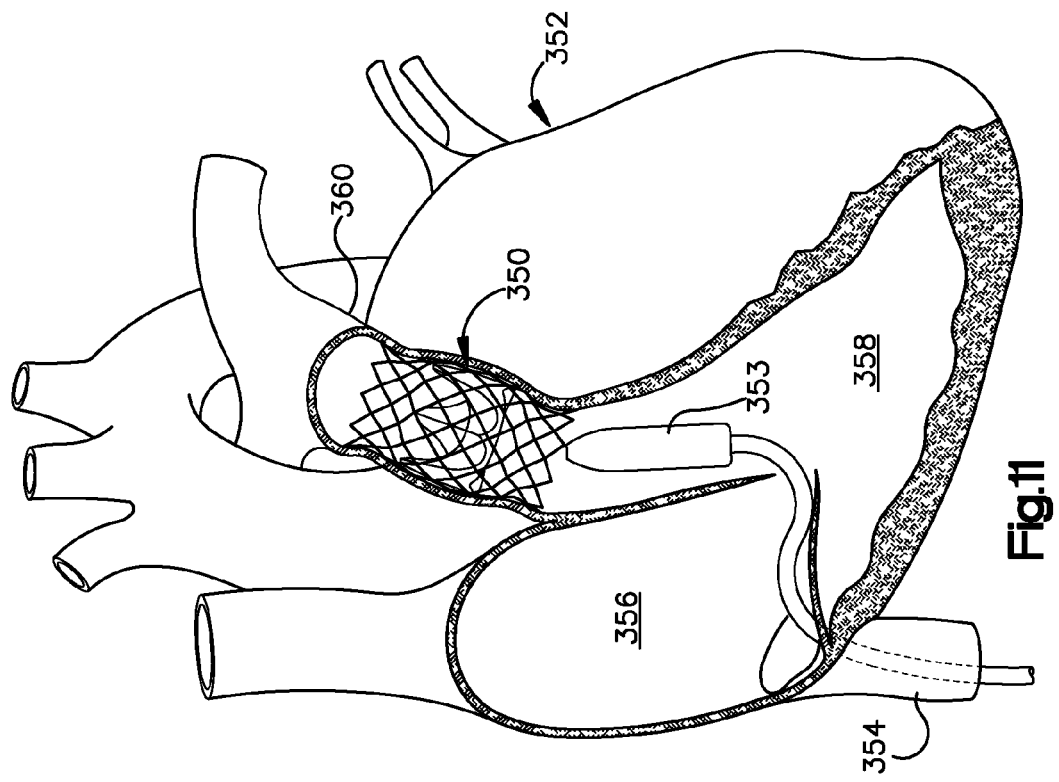
FIG. 11 is an example of a valvular prostheses implanted in a pulmonic position of a heart in accordance with the present invention.

FIG. 11 illustrates an example of a valvular prosthesis 350 implanted in a pulmonary position of a heart 352. The particular example illustrated in FIG. 11 shows an enclosure 353, such as may be part of a catheter, which has been inserted into the heart 352 to place the prosthesis at a desired position. Specifically, the catheter has traveled through the inferior vena cava 354, into the right atrium 356 and into the right ventricle 358 to position the valvular prosthesis 350 at a desired position relative to the pulmonary artery 360.

As mentioned above, the prosthesis 350 is mounted within the enclosure 353 in a compressed condition prior to implantation. The enclosure 353 and the prosthesis 350, for example, may be introduced into the inferior vena cava through the patient's right femoral vein. The prosthesis 350 and enclosure 353 may traverse the vascular system to the inferior vena cava 354 with the assistance of suitable imaging equipment such as x-ray, ultrasound, or other imaging devices. The imaging equipment is utilized to navigate the enclosure 353 and the prosthesis 350 to the desired position. Once at the desired position, such as at the opening to the pulmonary artery 360, the prosthesis 350 may be discharged through a distal opening of the enclosure 353. The valvular prosthesis 350 then expands from its compressed condition to an expanded condition, as illustrated in FIG. 11. Advantageously, when the valvular prosthesis 350, which is formed of an elastic material (e.g., nitinol in its heated form), is urged through the opening of the enclosure 353, it will automatically expand and dilate, thereby also expanding the valve that is attached to the stent. Therefore, the valvular prosthesis 350 becomes functional almost immediately. The enclosure 353 may then removed out of the heart 352, through the inferior vena cava 354 and removed from the patient.

Advantageously, the valvular prosthesis 350 may be implanted in the patient without cardiopulmonary bypass. As a result, a significant amount of time may be saved with less stress on the patient, thereby mitigating the risks of morbidity and mortality associated with conventional open-heart surgery typically employed to implant a heart valve prosthesis. Those skilled in the art will understand and appreciate that this process also may be utilized to implant a valvular prosthesis for a venous valve, such as in a patient's lower limb.

FIG. 12 illustrates another support structure 400 that can be employed as part of a heart valve prosthesis in accordance with an aspect of the present invention. The support 400 has a generally cylindrical configuration that extends between spaced apart ends 402 and 404. A plurality of interconnected support features 406 extend generally axially between the ends 402 and 404. The support features 406, for example, are formed of a length of a resilient rod or wire (e.g., nitinol, surgical steel, aluminum, a polymer, and the like). Biasing elements 408, such as coil springs, interconnect at least some of the support features 406 at the respective ends 402 and 404. The biasing elements 408, for example, are arranged in a circular array spaced circumferentially apart from each other at the respective ends 402 and 404. The biasing elements 408 urge each pair features 406 interconnected by the respective biasing elements apart from each other in a circumferential direction. As a result of the circumferential expansion between features 406 imposed by the biasing elements 408, the cylindrical support 400 tends to expand radially outwardly. Additionally or alternatively, the support 400 can be integrally formed from a single piece of material configured to a desired shape and configuration. For example, such an integral structure can be formed via laser ablation from a tube a suitable from a metal, such as nitinol.

The support 400 also includes one or more retaining elements 410 that inhibit radial expansion of the support beyond a certain desired amount defined by the length of the retaining elements 410. For example, the retaining element 410 can be in the form of one or more flexible cords (e.g., sutures) that limit circumferential expansion of the features 406 caused by the biasing elements 408. In the example in FIG. 12, cords are in the form of flexible loop of material attached to the biasing elements 408 located at each end 402, 404 of the support 400. The cords further are threaded through apertures of each of the biasing elements, although the cords could be connected at the ends 402 and 404 by other attachment arrangements. For example, one or more cords could be threaded between adjacent support features an axial location between the ends 402 and 404. Alternatively, other types of flexible retaining mechanisms (e.g., a strip of treated animal tissue, fabric, etc.) could be attached to the support 400 to limit its circumferential expansion, although still permit a desired reduction in its cross-sectional dimension.

FIG. 13 illustrates another example of a generally cylindrical support structure 420 that could be used to form a heart valve prosthesis in accordance with an aspect of the present invention. The support 420 is similar to the support shown and described with respect to FIG. 12 and, for example, can be formed of the same or similar materials, as described with respect to FIG. 12. Briefly stated, the support includes a cylindrical intermediate portion 422 having spaced apart ends 424 and 426. The intermediate portion 422 includes a plurality of interconnected support features 428 that extend generally axially between the ends 424 and 426. At least some of the features 428 are interconnected with adjacent features by biasing elements 430 located at the juncture between adjacent interconnected features. While the biasing elements 430 are illustrated as being located at the ends 424 and 426, it is to be understood and appreciated that they alternatively could be located between adjacent features at a different axial position (e.g., intermediate) somewhere between an adjacent pair of features in accordance with an aspect of the present invention.

The support 420 also includes retaining features 432 that limit the circumferential expansion of the support to a desired amount. The retaining feature 432 is in the form of a pair of cords (e.g., sutures) having ends connected together to form a loop that is connected at each end 424 and 426 of the support. Each loop 432 is flexible to permit the support to be deformed into a reduced cross-sectional dimension. The loops 432 also inhibit expansion at each of the ends 424 and 426 according to the dimensions of the respective loops. For example, one end 426 (e.g., the inflow end) can have a larger maximum diameter than the other end 424 (e.g., the outflow end) of the intermediate portion 422.

The support 420 further includes members 440 and 442 that extend axially and radially outwardly from the respective ends 424 and 426 of the support. In this example, each of the members 440 and 442 includes a plurality of triangular projections 444. Each projection 444 includes a pair of legs 446 that are connected to the respective ends 440 and 442. The legs 446 extend radially axially and radially outwardly from the respective ends 440 and 442 and terminate in an apex 448 spaced apart from the intermediate portion 422.

In the example in FIG. 13, each triangular projection 444 has a width that approximates the width of an elongated triangle formed of a pair of adjacent elongated features 428 of the intermediate portion 422. Each projection can have an axial length that is quite less than intermediate portion. Adjacent triangular projections 444 are coupled together at the ends 424 and 426 by additional biasing elements 450. The apex 448 also includes a similar biasing element 452, which further tends to urge respective legs 446 apart from each other. Thus, the biasing elements 450 and 452 of the triangular projections cooperate with the biasing elements 430 of the intermediate portion to increase the associated radially expansive force of the support 420. As mentioned, however, the dimensions of the retaining feature 432 can limit the radial expansion of the support 420. The projections 444 also provide a mechanism that can engage adjacent tissue, such as when implanted in a patient's heart, so as to inhibit axial movement of the prosthesis relative to the heart. Each of the members 440, 442 and the intermediate portion 422 can be formed from a separate length of a generally resilient wire that connected together at the ends by the associated connecting elements 432, as shown in FIG. 13. While six symmetrical triangular projections are illustrated in FIG. 13, it is to be appreciated that other numbers and shapes of projections could be used in accordance with an aspect of the present invention.

FIGS. 14 and 15 illustrate an example of a heart valve prosthesis 470 in accordance with an aspect of the present invention. The prosthesis 470 is particularly useful during a direct vision implantation, which can be sutureless, in accordance with an aspect of the present invention. The prosthesis 470 includes a heart valve 472 mounted within a support, such as the support 420 of FIG. 13, which can expand from a reduced cross-sectional dimension to an expanded condition as shown. Identical reference numbers refer to parts of the support 420 previously identified with respect to FIG. 13. It is to be understood and appreciated that other deformable, self-expanding supports also can be utilized in accordance with an aspect of the present invention.

The valve 472 includes an inflow end 474 and an outflow end 476 at axially opposed ends of the valve, with a sidewall portion 478 extending between the ends thereof. The inflow end 474 of the valve 472 is positioned near an inflow end 426 of the support 420. The sidewall portion 478 can be a tubular valve wall. A plurality of leaflets 480 extend radially inward from the valve wall 478 and coapt along their side edges to provide for substantially unidirectional flow of blood through the valve 472. The outflow end 476 of the valve 472, which is located near the outflow end 424, has a generally sinusoidal contour. The peaks are aligned with commissures between adjacent leaflets 480, with sinuses located between the commissures. The valve 472 can be connected within the support 420 via sutures 124 or other connecting means.

By way of illustration, when the prosthesis is to be implanted at the pulmonary position, the valve 472 can be a treated porcine pulmonic valve. When it is to be implanted at an aortic position, the valve 472 can be a porcine aortic valve. For example, the valve can be of the type shown and described in U.S. Pat. Nos. 5,935,163, 5,861,028 or 5,855,602. It is to be understood and appreciated that other valve configurations of could be used in accordance with an aspect of the present invention. For example, one or more leaflets of the valve 472 could be mounted within a length of tubular valve wall or other generally cylindrical biocompatible material and operate in a known manner to provide for the unidirectional flow of fluid through the valve from the inflow to outflow ends.

In accordance with an aspect of the present invention, the prosthesis 470 also includes an outer sheath 482 of a substantially biocompatible material. The outer sheath 474 covers at least a substantial amount of exposed portions of the support 420 (including the ends 424 and 426) so as to mitigate contact between the blood and the support when the prosthesis is implanted. In the example of FIGS. 14 and 15, the outer sheath 482 covers the entire support, including the end portions 440 and 442 as well as the intermediate portion 422. The outer sheath 482, for example, is formed of one or more natural tissue sheets (e.g., animal pericardium), although other natural or synthetic biocompatible materials also could be used to provide an outer sheath in accordance with an aspect of the present invention.

FIG. 16 illustrates another example of an elongated generally cylindrical support 500 that can be employed to support a heart valve in accordance with an aspect of the present invention. The support 500 generally consists of two cylindrical support portions 502 and 504, similar to the support of FIG. 12. The support portions 502 and 504 are connected together end-to-end in a substantially coaxial arrangement. For example, a length of a flexible cord 506 or other flexible retaining element connects adjacent ends of the respective support portions 502 and 504. The cord 506 has ends that are connected together to form a loop that determines a maximum diameter of the support 500 at the juncture between the two support portions 502 and 504. Other similar loops of flexible cords 508 and 510 are connected at opposite ends of the support 500 to inhibit expansion of the ends beyond a desired maximum diameter. The length of the cords 508 and 510 at the respective ends can be different so that one end (e.g., the inflow end) has a greater diameter than the other end (e.g., the outflow end).

The support 500 includes a plurality of generally axially extending features 512 (e.g., resilient rods or wires) that are biased to urge adjacent interconnected features circumferentially apart from each other. Because a plurality of such features are interconnected in a cylindrical arrangement, the biasing of the features apart from each other results in radially outward expansion of the cylindrical support 500 according to the dimensions of the retaining cords 506, 508, and 510. In one aspect, biasing elements 514, which can be springs, connect each adjacent pairs of features 512 together at each end of each respective support portion 502 and 504. Each of the cords 506, 508, 510 further interconnect a respective set of biasing elements at a corresponding axial location, with the cord 506 interconnecting biasing elements of both support portions at the intermediate axial location. While substantially identical biasing elements 514 are illustrating throughout the support 500, it is to be understood and appreciated that different types of biasing elements could be used at different locations of the support. Additionally, a separate length of a flexible cord can be used to interconnect adjacent support features, instead of the single loop inserted through an aperture of the respective biasing elements shown and described herein.

In view of the arrangement described above, it is to be appreciated that a length of the cord 506, 508 or 510 that extends between adjacent biasing elements 514 of each support portion 502, 504 and the pair of interconnected adjacent features 512 define a generally triangular structure. A plurality of such triangular structures are interconnected in a circumferential arrangement to define the generally cylindrical sidewalls of the respective support portions 502 and 504. The features 512 of each such triangular structure are urged apart from each other by the interconnecting biasing element 514. The juncture of the support portions 502 and 504 are connected by the connecting element 506 so as to provide radial expansion combined from both of the support portions. As a result, about twice the amount of radial expansive force is provided along the length of the cord 506.

The resulting support 500 thus provides a cage-like structure in which a valve can be mounted in accordance with an aspect of the present invention. The support 500 can be deformed to a reduced cross-sectional dimension, such as by applying a radially inward force to the sidewall portion thereof. Upon removal of the radially inward force, the support will expand to its expanded cross-sectional configuration due to the radial expansion provided by the arrangement of biasing elements 514 and interconnected axially extending features 512.

In accordance with an aspect of the present invention, FIG. 17 illustrates an example of a heart valve prosthesis 540 that includes a valve 542 mounted within a support 500, such as shown and described with respect to FIG. 16. Identical reference numbers refer to parts previously identified with respect to the support 500 of FIG. 16. The valve 542 has an inflow end 544 and an outflow end 546, which are positioned on axially opposed sides of the intermediate cord 506. In particular, the cord 506 and associated biasing elements 514 substantially circumscribe an annular base portion 548 of the valve 542 and help maintain it in a desired annular shape when the prosthesis 540 is in its expanded condition, as shown in FIG. 17.

The valve 542 illustrated in FIG. 17 includes three leaflets that extend radially inwardly from a length of trimmed valve wall so as to coapt and provide for the unidirectional flow of blood through the prosthesis from the inflow end 544 to the outflow end 546. The outflow end 546 has a generally sinusoidal contour, with peaks at the commissures between adjacent leaflets and sinuses between commissures extending an arc length commensurate with the arc length of the associated leaflet.

By way of illustration, when the prosthesis 540 is to be implanted at the pulmonary position, the valve 542 could be a treated porcine pulmonic valve and a porcine aortic valve when it is to be implanted at an aortic position. For example, the valve can be of the type shown and described in U.S. Pat. Nos. 5,935,163, 5,861,028 or 5,855,602. Of course, other types and valve configurations also could be used in combination with the support 500 to form the prosthesis 540 in accordance with an aspect of the present invention.

The prosthesis 540 further includes an outer sheath 550 of a flexible biocompatible material, such as treated and detoxified animal pericardium, as described herein. The outer sheath 550 covers at least some of the exposed support 500, such as the interior of the prosthesis and the ends 552 and 554. The outer sheath 550 can be formed of one or more sheets of the biocompatible material, which are attached to the prosthesis 540 to reduce exposure of the support to blood when implanted in its expanded condition. The outer sheath 550 is sufficiently flexible and resilient so as to facilitate deforming the prosthesis 540 to a reduced cross-sectional dimension and its subsequent expansion to its expanded cross-sectional dimension, as shown in FIG. 17.

The sidewall portion of the valve 542 is attached (e.g., by sutures) to the support 500, such as to features and/or biasing elements, so that when the support expands, the valve also expands to its desired expanded configuration. Also, because the valve 542 has been fixed (e.g., in a suitable glutaraldehyde solution) to a desired shape and configuration, the valve maintains its desired shape and coaptation between leaflets when the prosthesis 540 is in its expanded condition.

Prior to implanting the 540, such as by a direct implantation procedure through a blood vessel that provides a generally linear path to the desired implantation site, one or more sutures 554 can be attached to the proximal end 552 of the prosthesis. For example, the suture 554 is applied through loops that form generally diametrically opposed biasing elements 514 at the proximal end 552. The sutures 554 can be used to adjust the relative position of the prosthesis 540 after positioned in the heart in its expanded condition. Additionally or alternatively, the prosthesis 540 could be adjusted to a desired position manually by a surgeon by applying external force to the prosthesis through the heart. Advantageously, the prosthesis 540 can be directly implanted without cardiopulmonary bypass, such as in the pulmonary position or with minimal bypass to the aortic position in accordance with an aspect of the present invention.

Figure 18:
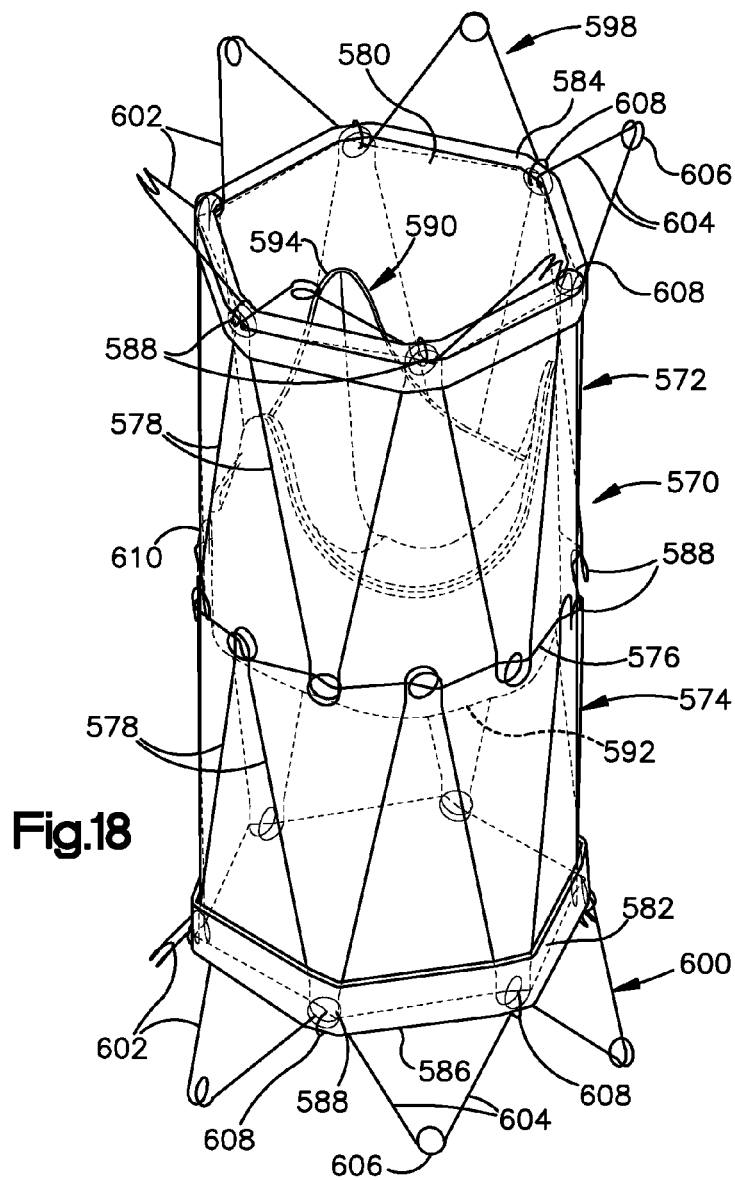
FIG. 18 is an example of a heart valve prosthesis employing a support structure in accordance with an aspect of the present invention.

FIG. 18 illustrates another example of a heart valve prosthesis 570 in accordance with an aspect of the present invention. The prosthesis 570 is similar to that show and described with respect to FIG. 17. Briefly stated, the prosthesis 570 includes first and second generally cylindrical portions 572 and 574 that are connected together end to end by an intermediate flexible connecting element 576 having a desired diameter, such as a loop of a cord (e.g., suture). The connecting element 576 limits the radial expansion of an intermediate portion of the prosthesis to predetermined diameter.

Each of the cylindrical portions 572 and 574 includes a plurality of generally axially extending support features 578, such as thin rods, bands, or wire of a substantially resilient material. The features 578, for example, are arranged as a plurality of interconnected triangles in which the features define elongated legs that extend between the intermediate connecting element 576 and additional connecting elements 580 and 582 located at the opposite ends 584 and 586 of the associated cylindrical portions 572 and 574. The connecting element 582 at the inflow end of the valve also can have a greater diameter than the connecting element 580 at the outflow end. The features 578 in each cylindrical portion 572 and 574 are connected by biasing elements 588 that urge each adjacent pair of interconnected features circumferentially apart from each other. Because the features 578 are connected in a circumferential array, the collective forces of the biasing elements result in radially outward expansion of the prosthesis 570 up to a maximum dimension defined by the respective connecting elements 576, 580 and 582.

The prosthesis 570 further includes a heart valve 590 mounted within the support. The valve 590 has an inflow end 592 and an outflow end 594, which are positioned on axially opposed sides of the intermediate cord 576. In particular, the intermediate connecting element 576 and associated biasing elements 588 substantially circumscribe an annular base portion near the inflow end 592 of the valve 590. Because the valve 590 is attached (e.g., by sutures) to the support formed of the cylindrical portions 572 and 574, the radial outward forces provided by the support help maintain the base of valve in a desired annular shape when the prosthesis 570 is in its expanded condition shown in FIG. 18. When the inflow end of the valve 590 is in its desired annular shape, the leaflets of the valve also are in desired orientation to provide desired coaptation between the leaflets, which facilitates the unidirectional flow of blood through the valve.

By way of example, when the prosthesis 570 is to be implanted at the pulmonary position, the valve 590 could be a treated porcine pulmonic valve. A porcine aortic valve can be used for the aortic position. Those skilled in the art will understand and appreciate other types and valve configurations also could be used in the prosthesis 570 in accordance with an aspect of the present invention.

The prosthesis 570 further includes an arrangement of members 598 and 600 that extend axially and radially outwardly from the respective ends 584 and 586 of the prosthesis 570. The members 598 and 600 are operative to help secure the prosthesis 570 to surrounding tissue when it is implanted.

The members 598 and 600 include a plurality of triangular projections 602 that extend axially and radially outwardly from the ends. While six substantially symmetrical projections are shown extending outwardly from each of the ends 584 and 586, those skilled in the art will understand and appreciate that any number could be used (e.g., 4, 6, 9, 12, 18, etc.).

Each triangular projection 602 includes a pair of legs 604 that are connected together by an interconnecting biasing element 606. The biasing elements form apices of the triangular projection 602 spaced from the respective ends 584, 586. Adjacent triangular projections 602 also are coupled together and to respective ends 584 and 586 by additional biasing elements 608 located at the ends of the prosthesis 570. The biasing elements 588, 606, and 608 bias the support portion of the prosthesis 570 and valve 590 attached thereto in a radially outward direction toward its fully expanded condition. Additionally, the triangular projections 602 can further engage surrounding tissue when the prosthesis is implanted to help hold the prosthesis at a desired position relative to the surrounding tissue.

The prosthesis 570 also can include an outer sheath 610 of biocompatible material (e.g., animal pericardium) that covers most (or all) of the support structure that would be exposed to blood when implanted. The covering further could be an expansion of the valve wall the contains the leaflets of the heart valve 590. In this example, the outer sheath 610 covers the support between the ends 584 and 586 of the cylindrical portions 572 and 574 and the support features 578 in the interior of the prosthesis 570. The triangular projections 602 are left uncovered, which may facilitate their insertion and integration into surrounding tissue. It is to be understood and appreciated, however, that the projections 602 also could be covered with biocompatible material, similar to the example of FIGS. 14 and 15.

The prosthesis 570 is well suited for direct implantation without cardiopulmonary bypass, such as in the pulmonary position, or direct implantation with minimal bypass to the aortic position in accordance with an aspect of the present invention. Direct implantation with the prosthesis also can be sutureless, although one or more sutures can be applied to further fix the prosthesis at a desired position.

In view of the various arrangements of heart valve prostheses described herein, a simplified and efficient method of using such prosthesis is described below with respect to FIGS. 19-22. The prosthesis can be directly implanted into the patient's heart in an efficient and low-invasive procedure, which also can be sutureless. While the particular example utilizes a heart valve prosthesis similar to that shown and described in FIG. 18, it is to be understood and appreciated that any of the prosthesis (see, e.g., FIGS. 1-18) described herein, could be implanted in a similar manner.

Figure 19:
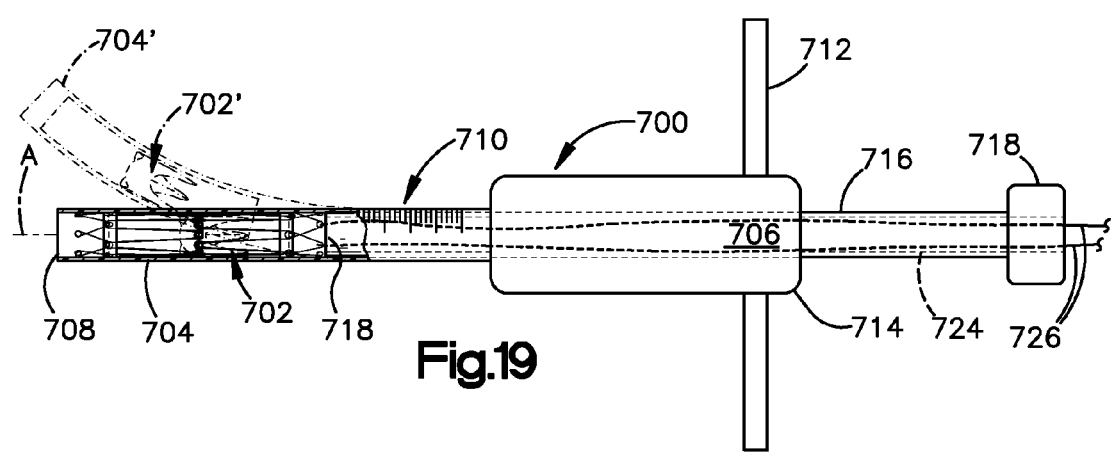
FIG. 19 is an example of an implanter apparatus for implanting a prosthesis in accordance with an aspect of the present invention.
Figures 20, 21:
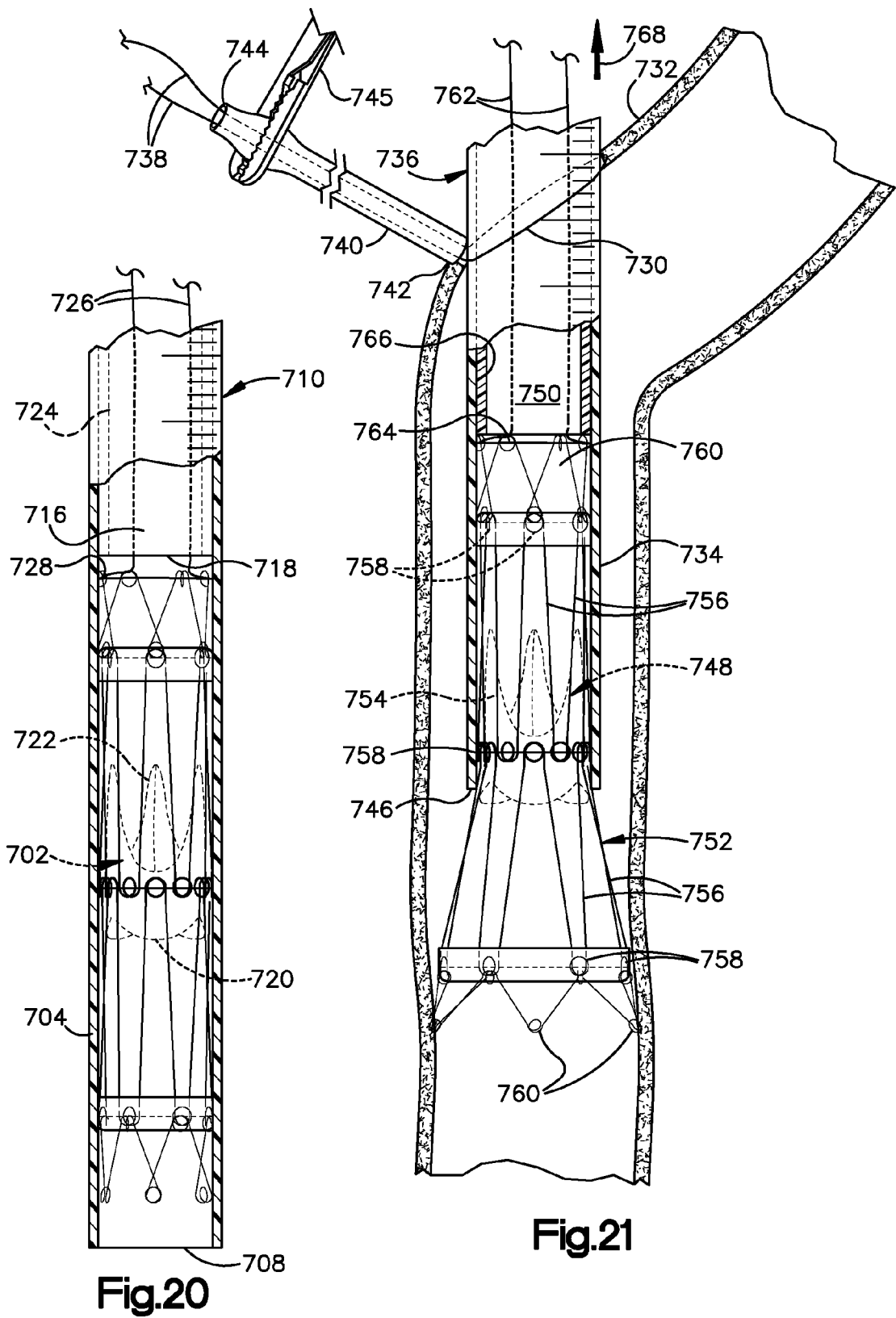
FIG. 20 is an enlarged view of part of the implanter apparatus of FIG. 19.
FIG. 21 is an example of a prosthesis being implanted at a desired location in accordance with an aspect of the present invention.

FIGS. 19 and 20 illustrates an implanter apparatus 700 for implanting a heart valve prosthesis 702 in accordance with an aspect of the present invention, such as to facilitate sutureless implantation under direct vision of the surgeon. The implanter 700 includes an elongated cylindrical barrel 704 that extends from a body portion 706 and terminates in an open end 708. The barrel 704 has an inner diameter that is less than the outer diameter of the heart valve prosthesis 702 in its expanded condition. Thus, in order to facilitate insertion of the prosthesis 702 into the barrel 704, the prosthesis should be deformed to a reduced cross-sectional dimension, such as at about one-half or less of its fully expanded condition, as shown in the enlarged view of FIG. 20.

For example, the inner diameter of the barrel 704 can range from about 5 mm to about 15 mm, whereas the outer diameter of the heart valve prosthesis 702 (in its expanded condition) typically ranges from about 15 mm to about 35 mm. Thus, the barrel can accommodate a prosthesis 702, which has been deformed to reduced cross-sectional dimension, without compromising the durability and operation of the valve. The exterior of the barrel further can include indicia (e.g., ruler markings) 710 that can help indicate the distance the barrel is inserted into a patient.

Additionally, to facilitate positioning the end 708 of the barrel 704 at a desired position, such as in a patient's heart, the barrel 704 (or at least a distal end portion thereof) can be formed of a flexible, generally resilient material (e.g., a metal or plastic material) that can bend or flex relative to its longitudinal axis A, as indicated at 704'. By way of particular example, the barrel 704 can be formed of helical extension spring, such as formed of a thin wire tightly wound to defines the circular cylindrical barrel in which the heart valve prosthesis can be loaded for implantation. The barrel 704 thus can flex to a curved or bent position 704', such as to accommodate different angular contours that might be experienced in various passages in the patient's heart as the barrel 704 is guided to a desired implantation position. Such compliant tensile properties of the barrel 704, for example, facilitate gently deflecting the barrel off anatomical structures during implantation, such as the barrel is advanced to its implantation position.

Alternatively or additionally, the barrel 704 can be formed of a deformable material, such as synthetic material (e.g., a polymer) or a metal, that can be deformed to provide a desired curved barrel 704' for supporting the heart valve prosthesis 702' for implantation. Accordingly, the barrel 70 can be curved or bent relative to the longitudinal axis A of the implanter 700, as indicated at 704'. For example, those skilled in the art will understand and appreciate various suitable materials that could be utilized to provide desired flexible and/or deformable properties.

The implanter 700 also includes a handle 712 that extends outwardly from a proximal end 714 of the body portion 706. The handle 712, which may be gripped by a surgeon, facilitates manipulating the barrel 704 along a desired path. A plunger 716 has a distal end 718 that can be urged into engagement with the prosthesis 702 to push the prosthesis from the opening 708 of the barrel 704. The plunger 716 includes an elongated portion that extends from its distal end 718 and terminates in a proximal end portion 718. The proximal end portion 718 operates as a trigger that can be grasped by a surgeon to move the plunger through the barrel 704. Other means to discharge the heart valve also could be utilized in accordance with an aspect of the present invention. Fluid, such as saline, also can be introduced into the barrel 704, such as through an opening (not shown) in the plunger 716, to facilitate the discharge of the prosthesis 702 from the barrel.

In the examples of FIGS. 19 and 20, the heart valve prosthesis 702 is positioned within the barrel 704 with its inflow end 720 adjacent to the outflow end, such as for implanting the valve in a pulmonary position. Those skilled in the art will understand and appreciate that the outflow end 722 of the valve 702 alternatively could be positioned adjacent the opening 708 of the barrel. The particular orientation of the valve 702 within the barrel 704 will depend on where the valve is being implanted and the direction from which the implanter 700 is being inserted relative to the implant site. In accordance with a particular aspect of the present invention, the implanter 700 and heart valve prosthesis 702 is particularly useful for an open chest procedure in which the prosthesis is introduced into the heart under substantially direct vision of the surgeon.

For example, the implanter 700 could be introduced into a blood vessel (e.g., the pulmonary artery) that provides a substantially direct and linear path to the desired implantation position. Further, the procedure can be implemented without cardiopulmonary bypass, such as when the prosthesis is implanted through the pulmonary artery. Alternatively, cardiopulmonary bypass can be used, but for a generally short period of time, such as when the prosthesis is implanted at the aortic position. Bypass generally is required when implanting at the aortic position due to the relatively high blood pressure as well as to facilitate decalcification of the patient's existing heart valve, as needed.

The implanter 700 further can include an aperture 724 (or interconnected apertures) that extend longitudinally through the plunger 716 and the end 718. The aperture 724 provides a passage through which one or more sutures 726 connected to a proximal end 728 of the prosthesis 702 can extend. For example, prior to loading the prosthesis 702 into the barrel 704, the suture 726 can be applied to the end 728 of the prosthesis, such as through generally diametrically opposed biasing elements (e.g., coil springs) at the respective end. Part of the suture 726 extends between the opposed sides of the prosthesis 702. The remaining lengths of the suture 726, which extends from one or both sides of the prosthesis, can be fed through the barrel and aperture 724 to a location external to the implanter 700, such as shown in FIG. 19. The suture 726 should have a sufficient length to extend through the implanter 700, as shown. After the prosthesis 702 has been discharged from the implanter, the suture 726 then can be grasped by a surgeon to adjust the position of the prosthesis.

FIG. 21 illustrates an intermediate part of an implantation procedure in accordance with an aspect of the present invention. In this example, cardiopulmonary bypass is not required, as blood loss is mitigated through application of a purse string suture. For example, after the patient's chest is opened, a purse string suture 730 is applied to the pulmonary artery or other vessel 732 through which a barrel 734 of an implanter 736 is to be inserted. A small incision or puncture is made at the center of the purse string 730, which should approximate or be slightly smaller than the outer diameter of the barrel. Alternatively, the incision could be made prior to application of the purse string to the vessel wall.

The surgeon can then insert the barrel 734 through the opening in the vessel wall 732. Two lengths 738 of the purse string 730 suture extend from the vessel 732 through an elongated cylindrical guide 740 of a generally rigid material, such as rubber, plastic, or metal material. One end 742 of the cylinder 740 engages the vessel wall 732 and/or the barrel 734, and the two lengths 738 of suture extend through the other end 744. By fixing the length of suture relative to the cylinder 740, such as by clamping the sutures to the cylinder by a clamp 745, the vessel wall surrounding the barrel 734 can be kept relatively tight around the barrel so as to mitigate blood loss through the incision. As a result, cardiopulmonary bypass is not required. However, it is to be understood that in certain situations, such as when implanting the prosthesis at the aortic position, some bypass may be necessary, although usually for a much shorter period of time than with conventional procedures.

After the distal end 746 of the barrel 734, which can be flexible or bendable as described herein, has been inserted a desired length into the vessel 732, such as indicated by indicia printed on the barrel, the heart valve prosthesis 748 located in the barrel can be discharged. For example, a plunger 750 positioned for axial movement relative to the barrel 734 can be moved toward the distal end 746 of the barrel and into engagement with the prosthesis 748. The heart valve prosthesis 748 is configured to expand toward its fully expanded condition when it is discharged from the barrel 734 because radial inward forces that maintain the prosthesis at a reduced cross-sectional dimension are removed. In particular, the prosthesis 748 includes a self-expanding support 752 in which an associated heart valve 754 is mounted. In the example of FIG. 21, the support 752 and valve 754 are configured as shown and described in FIG. 18. That is, the support 752 includes a cage-like frame of axially extending resilient support features 756 interconnected by biasing elements 758 that urge the support in a radially outward direction. Generally triangular projections 760, which also are biased radially outwardly, further extend from the ends of the support 752. The triangular projections 760 operate to engage the surrounding valve wall (or other surrounding tissue) when the support expands so as to anchor the prosthesis 748 relative to the valve wall. As the prosthesis 748 is being discharged, the implanter barrel 734 can be concurrently withdrawn from the vessel to help ensure that the prosthesis is positioned at the desired position.

One or more sutures 762 can be attached to a proximal end 764 of the prosthesis 748 so as to pass through an aperture 766 that extends through at least a substantial portion of the implanter 736. For example, the suture 762 can be applied through the centers of generally opposed circular biasing elements located at the proximal end 764. After the prosthesis 748 is discharged into the patient's heart, a surgeon can grasp the sutures to adjust the position of the prosthesis, such as by urging both ends of the suture in the direction 768, shown in FIG. 21. Additionally or alternatively, the relative position of the discharged prosthesis 748 can be adjusted through the heart or blood vessel manually or by employing other tools. Once the prosthesis 748 is at a desired position, one end of the suture can be pulled so as to remove the suture from the prosthesis. The adjustments can be performed with part of the implanter 736 still within the blood vessel 732 or after the implanter has been removed from the vessel.

Figure 22:
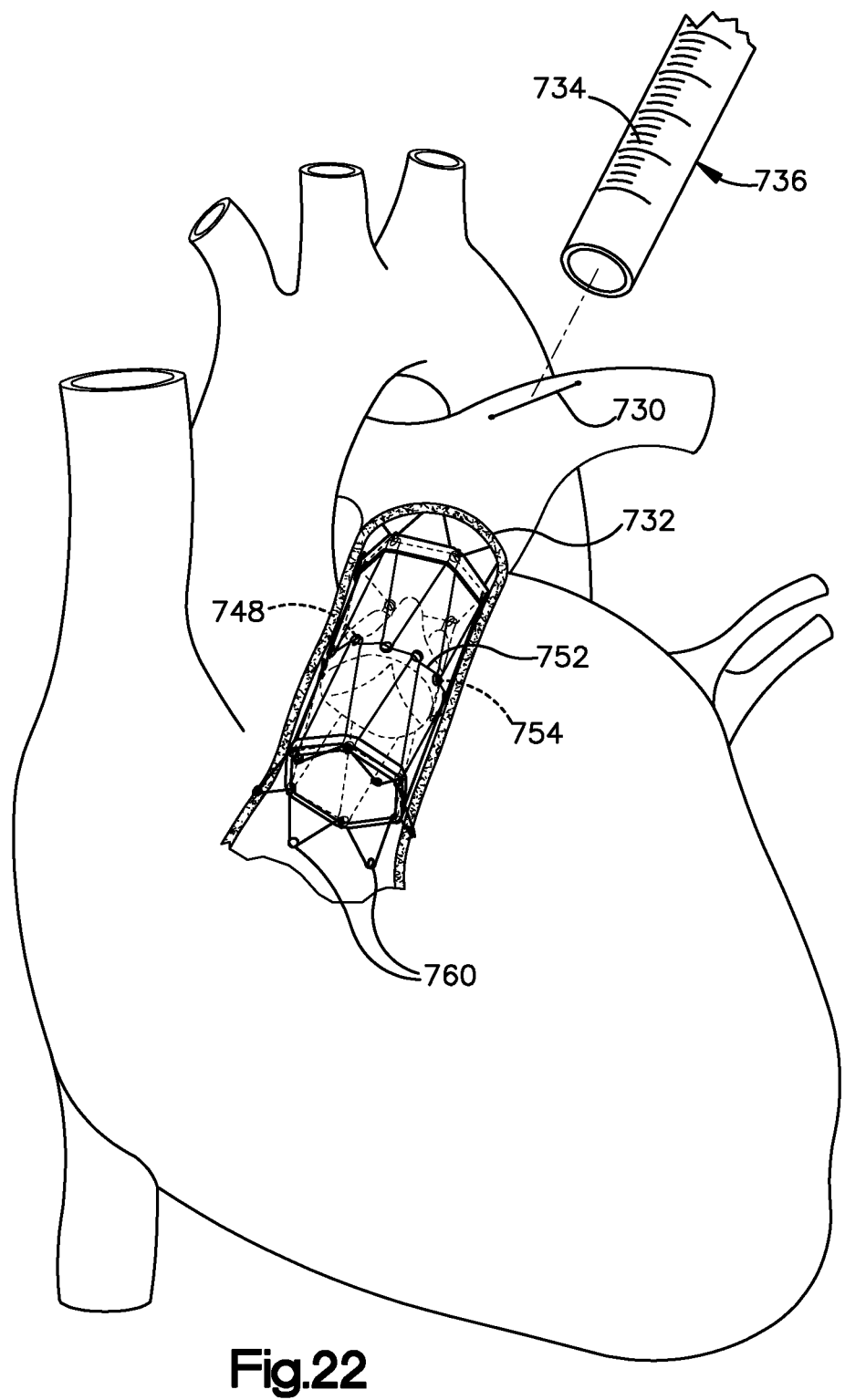
FIG. 22 is an example of a prosthesis mounted at a pulmonary position of a patient's heart in accordance with an aspect of the present invention.

FIG. 22 illustrates the heart valve prosthesis 748 mounted at a pulmonary position after the implanter 736 has been removed from the pulmonary artery 732 through which the prosthesis 748 was implanted in accordance with an aspect of the present invention. As described herein, the barrel 734 can be generally rigid, flexible or deformable, such as part of a catheter or other type of implanter. After the barrel 734 of the implanter 736 has been withdrawn from the pulmonary artery 732, the purse string 730 facilitates closure of the incision. For example, the guide 740 (FIG. 21) can be held against the pulmonary artery 732 while concurrently pulling additional length of the suture 738 through the cylinder 740 and then tying off the purse string at the pulmonary artery. Additional sutures can be applied to the incision site to ensure proper closure. With the projections 760 engaging surrounding tissue and the outward force of the support 752, the prosthesis 748 should be adequately anchored at the desired position. Although, to help ensure that the prosthesis remains at the desired position, one or more sutures also can be applied to the prosthesis, such as directly through the heart muscle itself. The support 752 further helps maintain desired coaptation between the leaflets by urging the inflow end of the valve toward a desired annular shape.

In view of the foregoing example, those skilled in the art will understand and appreciate that the prosthesis 748 can be implanted without opening the heart and without cardiopulmonary bypass. When the patient's existing valve needs to be removed and or calcium deposits cleaned, such cleaning can be performed through the pulmonary artery or other connecting vessels prior to implanting the prosthesis 748, such as through a trocar and/or by endoscopic means.

Figure 23:
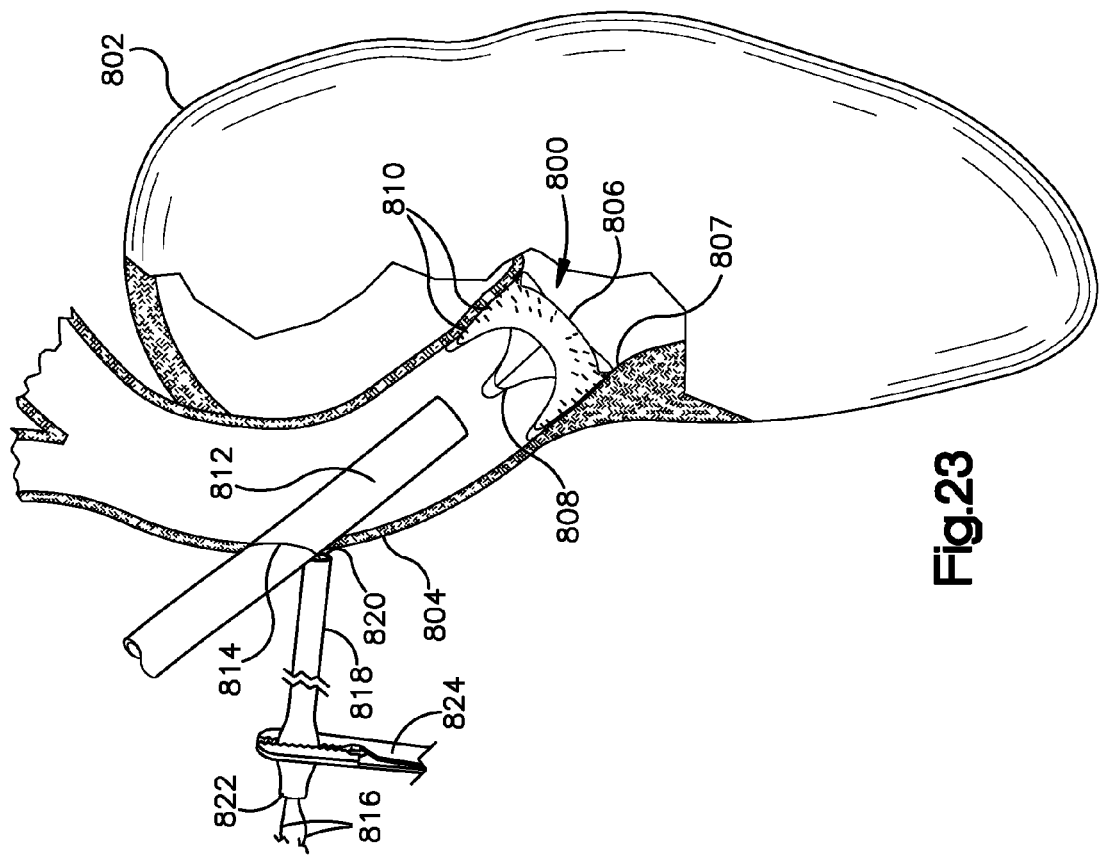
FIG. 23 is an example of a valve being implanted at the aortic position in accordance with an aspect of the present invention.

FIG. 23 depicts an example of a valvular prosthesis 800 being implanted in a patient's heart 802 at an aortic position according to an aspect of the present invention. When being implanted at an aortic position, an aortic valve (e.g., equine, porcine, bovine, etc.) can be utilized for the valve portion of the prosthesis, although other types of valve portions also could be used. Prior to implanting the prosthesis 800, the patient's own aortic valve or at least calcified portions thereof should be removed.

In this example, the prosthesis 800 is being implanted through the patient's aorta 804. The prosthesis includes can include an inflow end 806 that is positioned at the aortic annulus 807, with an outflow end 808 of the prosthesis extending into the aorta 804. As described herein, the implantation can be sutureless since the prosthesis 800 includes spikes or other projections 810 that extend outwardly from the prosthesis. Such spikes or protrusions 810 thus engage surrounding tissue, such as the aortic valve wall 804, for inhibiting axial and rotational movement of the implanted prosthesis 800, as described herein.

In the example of FIG. 23, the prosthesis 800 is implanted at the aortic position from the barrel 812 of an implanter. The implanter can be a catheter type of implanter in which the barrel is dimensioned to retain the prosthesis in a compressed condition during insertion through the aorta 804. After the distal end of the barrel is at a desired position, the valvular prosthesis 800 is discharged to its expanded condition. The barrel 812 can be flexible, deformable or generally rigid, as described herein.

It is to be appreciated that the valvular prosthesis 800 may be implanted in the aortic position during a conventional open chest procedure or during a closed chest procedure. In the example of FIG. 23, the barrel 812 can be urged through a small incision made in the aorta 804. Because the only incision is in the patient's aorta, the implantation can be performed during very short open chest surgery, for example, with reduced cardiopulmonary bypass when compared to conventional procedures.

The implantation can be performed in a manner similar to that described above with respect to FIG. 21. For example, after the patient's chest is opened, a purse string suture 814 is applied to the aorta 804, through which a small incision or puncture is made for inserting the barrel 812. Ends 816 of the purse string 814 are inserted through a hollow guide element 818. A distal end 820 of the guide element 818 is urged against the aorta 804 and the barrel 812, and a proximal end 822 is extended away from the heart 802. The ends 816 of the purse string suture are pulled through the guide element 818 and can be fixed relative to the guide, such as by clamping the sutures to the guide with a clamp 824. As a result, the vessel wall surrounding the barrel 812 can be kept relatively tight around the barrel so as to mitigate blood loss through the incision during the procedure. As a result, cardiopulmonary bypass can be kept at a minimum with little blood loss.

It is to be understood and appreciated, though, if the patient has a calcified aortic valve, the patient typically must be put on cardiopulmonary bypass to remove the calcium and implant the valve. Advantageously, a valvular prosthesis 800 in accordance with the present invention may be implanted more efficiently so as to mitigate morbidity and mortality of the patient. In addition, the prosthesis 800 can be implanted without sutures (or, alternatively, some sutures can be utilized. For example, optional sutures (not shown) may be applied near the inflow end 806 and/or at the outflow end 808, such as when the prosthesis is configured to have axially extending lobes (see, e.g., FIG. 8).

Figure 24:
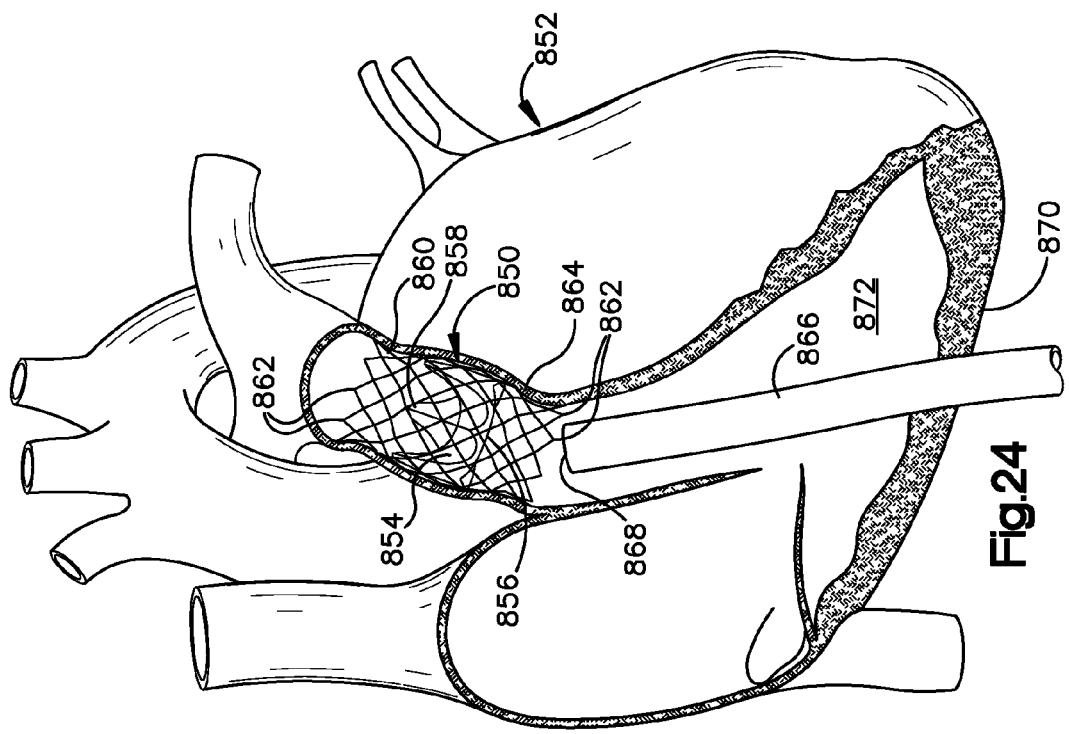
FIG. 24 is an example of a valve being implanted at the pulmonic position in accordance with an aspect of the present invention.

FIG. 24 illustrates an alternative approach for implanting a heart valve prosthesis 850 at the pulmonic position in a patient's heart 852 in accordance with an aspect of the present invention. As described herein, the prosthesis 850 includes a valve portion 854 having an inflow end 856 and an outflow end 858 spaced therefrom. The valve portion 854 can be a natural tissue heart valve, such as a homograft or xenograft, although other types of natural tissue heart valves also could be utilized, such as described herein. The valve portion 854 is mounted within a support or stent 860, such as one of the types described herein. The support 860 includes spikes or protruding portions 862 for engaging surrounding tissue of the pulmonary artery 864 in its implanted position. The protruding portions 862 thus inhibit axial and/or angular movement of the implanted prosthesis 850.

In this example, the prosthesis 850 is implanted into the pulmonary artery 864 from a barrel 866 of an implanter, such as a catheter system or other type of implanter described herein. In particular, a distal end 868 of the barrel is inserted through the heart muscle itself, such as through the anterior wall 870 of the right ventricle 872. Once at the desired position, the prosthesis 850 is ejected from the barrel 866 into the outflow of the right ventricle 872, as illustrated in FIG. 24. By entering through the anterior wall 870, a substantially direct or generally linear implantation can be performed with little or no cardiopulmonary bypass. Those skilled in the art will understand and appreciate other possible paths through the heart that could be employed for positioning the distal end 868 of the barrel 866 to facilitate sutureless implantation of a heart valve prosthesis in accordance with an aspect of the present invention.

Figure 25:
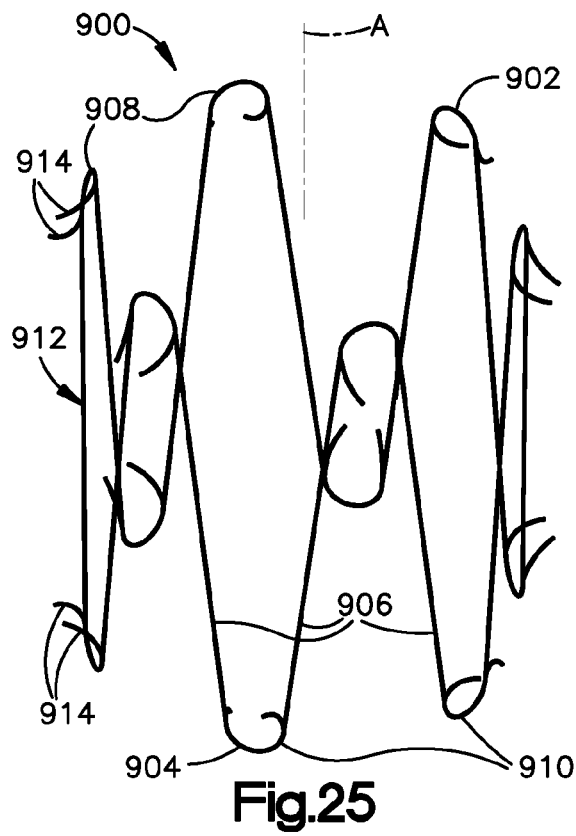
FIG. 25 is an example of another type of support structure in accordance with an aspect of the present invention.

FIG. 25 depicts an example of another type of support structure 900 that could be used to support a heart valve to provide a prosthesis in accordance with an aspect of the present invention. The support 900 includes axially spaced apart ends 902 and 904 interconnected by generally axially extending support features 906. In the example of FIG. 25, adjacent support features 906 are interconnected by arcuate junctures 908 and 910 at the respective ends 902 and 904 so as to define a generally sinusoidal sidewall portion 912 arranged in a generally cylindrical configuration. In the example of FIG. 25, there are six junctures 908 and 910 at each of the respective ends 902 and 904 that are interconnected by associated support features 906. Those skilled in the art will understand and appreciate that other numbers (e.g., 2, 3, 9, 12 and so forth) and configurations of end junctures 908, 910 can be utilized in accordance with an aspect of the present invention. For example, as an alternative to curved interconnecting end junctures 908, 910 shown in FIG. 25, such ends could be pointed or rectangular.

The support 900 further includes one or more projections or spikes 914 that extend axially and radially outwardly from at least some of the respective end junctures 908, 910 of the support. While a pair of such spikes are illustrated as associated with each end juncture 908, 910, other number of spikes can be implemented, such as single spike or more than two spikes at some or all of the junctures. In the example illustrated in FIG. 25 the pairs of spikes at opposite ends operate to mitigate movement in different directions, such as by having each spike 914 forming an acute angle relative to its associated support feature 906 from which it extends.

According to one aspect of the present invention, the support can be formed a shape memory material, such as nitinol. For example, the support can be formed from a small cylindrical tube of the shape memory material, such as via a laser cutting (ablation) process in which the desired sinusoidal sidewall 912 is cut from the tube. In this way, the support features 906, the interconnecting end junctures 908 and 910, and associated spikes 914 can be formed as an integrated structure having a desired shape and size. Additionally, ends of the spikes 914 can have tapered or sharpened tips to facilitate gripping surrounding tissue when implanted. For example, the spikes 914 can be formed by laser cutting from the same tube or, alternatively, they could be welded onto the support 900 at desired positions. The resulting structure can then be heated to its transformation temperature and forced to a desired cross-sectional dimension and configuration (its austenic form), such as shown in FIG. 25. The support 900 can then be bent or deformed to a reduced cross-sectional dimension when in its low-temperature (martensitic) form to facilitate its mounting within a barrel of a implanter, for example.

Figure 26:
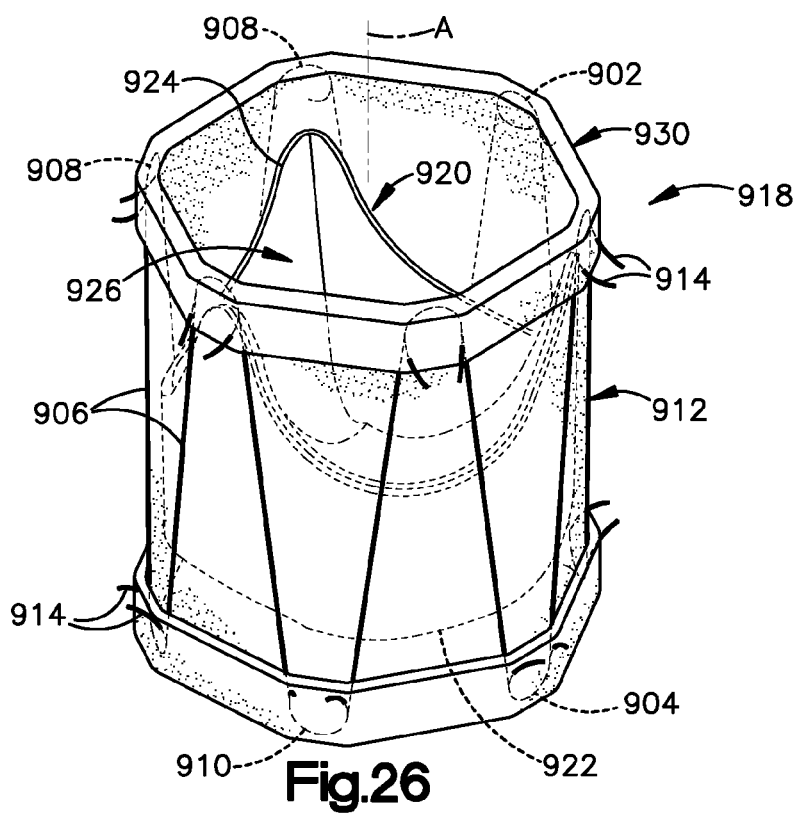
FIG. 26 is an example of a heart valve prosthesis employing the support structure of FIG. 26 in accordance with an aspect of the present invention.

FIG. 26 illustrates an example of a heart valve prosthesis 918 in accordance with an aspect of the present invention. The prosthesis 918 can be implanted during a direct vision implantation, which can be sutureless, in accordance with an aspect of the present invention. The prosthesis 918 includes a heart valve 920 mounted within a support, such as the support 900 of FIG. 25, which can expand from a reduced cross-sectional dimension to an expanded condition as described herein. Identical reference numbers refer to parts of the support 900 previously identified with respect to FIG. 25. It is to be understood and appreciated that other deformable, self-expanding supports also can be utilized in accordance with an aspect of the present invention.

The valve 920, which can be a homograft or xenograft, includes an inflow end 922 and an outflow end 924 at axially opposed ends of the valve, with a sidewall portion extending between the ends thereof. The inflow end 922 of the valve 920 is positioned near an inflow end 904 of the support 900. The prosthesis 920 also can include sidewall portion, which can be a tubular valve wall, such as for a homograft or xenograft valve 920. A plurality of leaflets 926 extend radially inward from the valve wall and coapt along their adjacent edges to provide for substantially unidirectional flow of blood through the valve 920. The outflow end 924 of the valve 920, which is located near the outflow end 902 of the support, has a generally sinusoidal contour, as shown in FIG. 26. The peaks of the sinusoidal outflow end 924 can be aligned generally with and attached to support junctures 908 at the end 902 of the support 900. The valve 920 can be connected within the support 900 via sutures or other known connecting means, for example.

It is to be understood and appreciated that various types of valve configurations of could be employed to provide the prosthesis 918 in accordance with an aspect of the present invention. For example, the valve 920 can include one or more leaflets mounted within a length of tubular valve wall or other generally cylindrical biocompatible material and operate in a known manner to provide for the unidirectional flow of fluid through the valve from the inflow to outflow ends. By way of further example, when the prosthesis is to be implanted at the pulmonary position, the valve 920 can be a treated pulmonic valve (e.g., homograft or xenograft). When it is to be implanted at an aortic position, the valve 920 can be a treated aortic valve (e.g., homograft or xenograft). For example, the valve can be of the type shown and described in U.S. Pat. Nos. 5,935,163, 5,861,028 or 5,855,602, as well as others mentioned herein or otherwise known in the art.

In accordance with an aspect of the present invention, the prosthesis 918 also includes an outer sheath 930 of a substantially biocompatible material. The outer sheath 930 covers at least a substantial amount of exposed portions of the support 900, such as including the ends 902 and 904, to mitigate contact between the blood and the support when the prosthesis is implanted. The valve 920 further can be attached relative to the sheath 930, such as by sutures along the inflow and outflow ends of the valve. Such sutures (not shown) further can connect the valve 920 and the sheath 930 relative to the support 900. The outer sheath 930 can cover the entire support, such that all non-biological material is completely covered, for example. The outer sheath 930 can be formed of one or more natural tissue sheets (e.g., animal pericardium), although other natural or synthetic biocompatible materials also could be used to provide an outer sheath in accordance with an aspect of the present invention.

Figure 27:
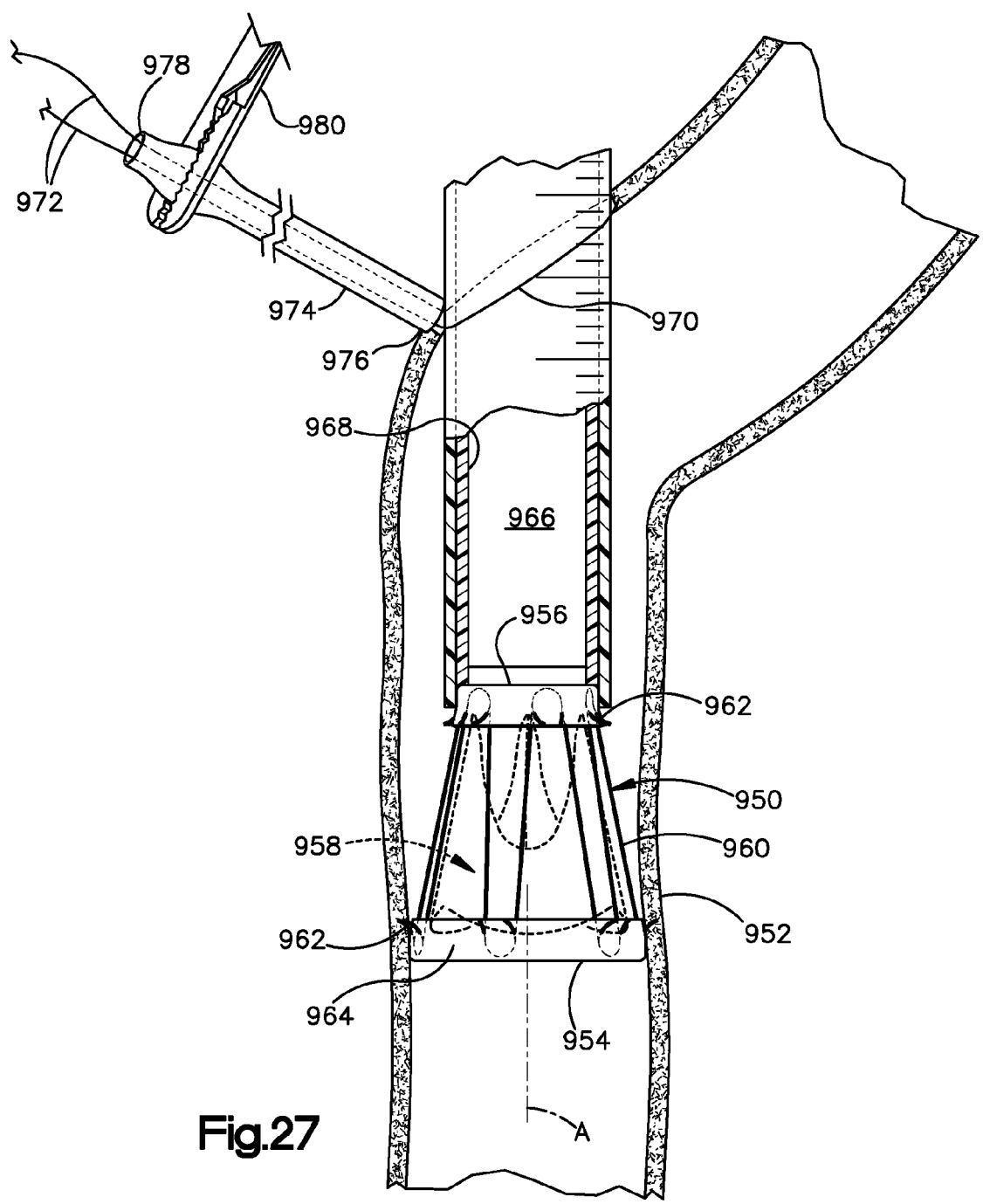
FIG. 27 is an example of a heart valve prosthesis being implanted in accordance with an aspect of the present invention.

FIG. 27 depicts an example of sutureless implantation of a heart valve prosthesis 950 being implemented in accordance with an aspect of the present invention. In this example, the prosthesis is illustrated of the type shown and described with respect to FIGS. 25 and 26. It will be appreciated that valve can be implanted within a vessel wall or other implantation site 952 without cardiopulmonary bypass or at least reduced bypass when compared to traditional approaches. The prosthesis 950 includes inflow and outflow ends 954 and 956 and a valve portion 958 mounted within a support 960 located between ends thereof. The support 960 includes spikes or protruding members extending outwardly from ends of the support. The spikes and support can be formed from an integral piece of a metal or alloy, such as nitinol, for example. A sheath 964 of biocompatible biological tissue (e.g., animal pericardium) covers at least a portion of the support to mitigate contact between fluid and non-biological portions of the prosthesis.

The implantation of the prosthesis 950 can be implemented in a manner similar to that show and described with respect to FIG. 21. Briefly stated, the prosthesis is ejected from a barrel 966 by a plunger 968 that is moveable axially within the barrel. To facilitate positioning the prosthesis 950 at a desired implantation site, the barrel 966 can be flexible, such as described herein, so as to gently deflect in response to contacting tissue along the passage toward to implantation site 952. Alternatively, the barrel can be deformable or generally rigid.

A small incision or puncture can be made at the center of a purse string 970 that is applied around the location through which the barrel 966 is to be inserted. The surgeon can then insert the barrel 966 through the opening in the vessel wall 952. Two ends 972 of the purse string 970 suture extend from the vessel wall or other tissue and through an elongated hollow guide 974. A distal end 976 of the guide 974 engages the vessel wall 952 and/or the barrel 966, and the two ends 972 extend through the other end 978. The suture can be fixed relative to the guide 974, such as by clamping the sutures to the cylinder by a clamp 980. As a result, the vessel wall (or other tissue) surrounding the barrel 966 can be kept relatively tight around the barrel to mitigate blood loss. Consequently, cardiopulmonary bypass is not required. However, it is to be understood that in certain situations, such as when implanting the prosthesis at the aortic position, some bypass may be necessary, although usually for a much shorter period of time than with conventional procedures.

As mentioned above, the prosthesis 950 includes a self-expanding support 960. Thus, the heart valve prosthesis 950 can expands toward its fully expanded condition when it is discharged from the barrel 966. The projections or spikes 962, in turn, will insert into surrounding tissue to maintain the valve at a desired axial and angular position in the vessel 952, thereby anchoring the prosthesis 950 relative to the valve wall. As the prosthesis 950 is being discharged, the implanter barrel 966 can be concurrently withdrawn from the vessel. While the implantation can be performed completely sutureless, those skilled in the art will understand and appreciate that one or more sutures can be utilized to further help secure the prosthesis 950 relative to the surrounding tissue 952.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" and variants thereof or the term "having" and variants thereof are used in either the detailed description or the claims, each such term is intended to be inclusive in a manner similar to the term "comprising."

What is claimed is:

1. A method for implanting a heart valve prosthesis into a patient's heart, the method comprising:
   inserting the heart valve prosthesis into a barrel of an implanter apparatus, such that the heart valve prosthesis has a reduced cross-sectional dimension relative to a fully expanded cross-sectional dimension of the heart valve prosthesis;
   creating an opening in tissue of the patient to provide a substantially direct path that extends from the opening to a desired implantation site in the patient's heart;
   introducing a length of the barrel through the opening in the tissue such that an end of the barrel and the opening are along the direct path to the implantation site;
   advancing the heart valve prosthesis through the barrel to the implantation site;
   positioning the heart valve prosthesis at the desired implantation site;
   expanding the heart valve prosthesis at the desired implantation site from the reduced cross-sectional dimension toward the expanded cross-sectional dimension, such that an exterior portion of the heart valve prosthesis engages adjacent tissue to mitigate movement of the heart valve prosthesis relative to the adjacent tissue.

2. The method of claim 1 wherein the opening is in a ventricle of the heart.

3. The method of claim 2 wherein the opening is made with a purse string suture.

4. The method of claim 2 wherein the implantation site is at an aortic valve.

5. The method of claim 2 wherein the implantation site is at a mitral valve.

6. The method of claim 2 wherein the implantation site is at a pulmonic valve.

7. The method of claim 2 wherein the implantation site is at a tricuspid valve.

8. The method of claim 2 wherein the positioning is performed using x-ray imaging.

9. The method of claim 2, 3, 4, 5, 6, 7 or 8 wherein the heart valve prosthesis is self expandable.

10. A method for implanting a heart valve prosthesis into a patient's heart, the method comprising:
    inserting the heart valve prosthesis into a catheter, such that the prosthesis has a reduced cross-sectional dimension corresponding to a dimension of the catheter, the heart valve prosthesis being configured to expand from the reduced cross-sectional dimension to an expanded cross-sectional dimension, which is greater than the reduced cross-sectional dimension;

creating an opening in tissue to provide a substantially linear path extending from the opening to a desired implantation position for replacing a heart valve in the patient's heart;

passing an open end of the catheter through the opening;

positioning the open end of the catheter adjacent the desired implantation position in the patient's heart such that the open end of the catheter and the opening are along the substantially linear path;

discharging the heart valve prosthesis from the catheter at the desired implantation position, whereupon the heart valve prosthesis expands from the reduced cross-sectional dimension to an expanded cross-sectional dimension, such that an exterior portion of the heart valve prosthesis engages adjacent tissue to mitigate movement of the heart valve prosthesis relative to the adjacent tissue.

11. The method of claim 10 wherein the opening is in a ventricle of the heart.

12. The method of claim 11 wherein the opening is made with a purse string suture.

13. The method of claim 11 wherein the implantation site is at an aortic valve.

14. The method of claim 11 wherein the implantation site is at a mitral valve.

15. The method of claim 11 wherein the implantation site is at a pulmonic valve.

16. The method of claim 11 wherein the implantation site is at a tricuspid valve.

17. The method of claim 11 wherein the positioning is performed using x-ray imaging.

18. The method of claim 11, 12, 13, 14, 15, 16 or 17 wherein the heart valve prosthesis is self expandable.

* * * * *